US011160802B2

(12) United States Patent
Xiong et al.

(10) Patent No.: US 11,160,802 B2
(45) **Date of Patent: *Nov. 2, 2021**

(54) COMPOSITION AND METHODS FOR PREVENTING OR REDUCING THE INCIDENCE OF TRANSIENT ISCHEMIC ATTACKS

(71) Applicant: MOREHOUSE SCHOOL OF MEDICINE, Atlanta, GA (US)

(72) Inventors: Zhigang Xiong, Atlanta, GA (US); Roger P. Simon, Atlanta, GA (US)

(73) Assignee: MOREHOUSE SCHOOL OF MEDICINE, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,055

(22) Filed: Feb. 14, 2020

(65) Prior Publication Data

US 2020/0188395 A1 Jun. 18, 2020

Related U.S. Application Data

(63) Continuation of application No. 16/114,815, filed on Aug. 28, 2018, now Pat. No. 10,603,316, which is a continuation-in-part of application No. 15/445,833, filed on Feb. 28, 2017, now Pat. No. 10,201,539, which is a continuation of application No. 13/972,558, filed on Aug. 21, 2013, now Pat. No. 9,629,838.

(51) Int. Cl.

| | |
|---|---|
| ***A61K 31/4965*** | (2006.01) |
| ***A61K 31/55*** | (2006.01) |
| ***C07K 14/435*** | (2006.01) |
| ***A61K 9/00*** | (2006.01) |
| ***A61K 31/155*** | (2006.01) |
| ***A61K 31/40*** | (2006.01) |

(52) U.S. Cl.

CPC ........ *A61K 31/4965* (2013.01); *A61K 9/0019* (2013.01); *A61K 9/0085* (2013.01); *A61K 31/155* (2013.01); *A61K 31/40* (2013.01); *A61K 31/55* (2013.01); *C07K 14/43518* (2013.01); *A61K 9/00* (2013.01)

(58) Field of Classification Search

None

See application file for complete search history.

(56) References Cited

U.S. PATENT DOCUMENTS

| | | | |
|---|---|---|---|
| 4,874,613 A | 10/1989 | Hsiao | |
| 5,753,702 A | 5/1998 | Bednar et al. | |
| 7,470,718 B2 | 12/2008 | Werner | |
| 10,201,539 B2 | 2/2019 | Xiong et al. | |
| 10,406,156 B2 | 9/2019 | Xiong et al. | |
| 10,603,316 B2 * | 3/2020 | Xiong | A61K 31/155 |
| 2006/0051319 A1 | 3/2006 | Yoo | |
| 2008/0242588 A1 | 10/2008 | Xiong et al. | |
| 2008/0279965 A1 | 11/2008 | Simon et al. | |
| 2009/0062309 A1 | 3/2009 | Delgado-Almeida | |
| 2011/0230552 A1 | 9/2011 | Gaudin et al. | |
| 2011/0312902 A1 | 12/2011 | Peterson | |
| 2012/0171697 A1 | 7/2012 | Kappel et al. | |
| 2013/0315897 A1 | 11/2013 | Sinha et al. | |
| 2014/0011817 A1 | 1/2014 | Xiong et al. | |
| 2016/0184304 A1 | 6/2016 | Xiong et al. | |

FOREIGN PATENT DOCUMENTS

| | | |
|---|---|---|
| EP | 0 451 130 | 10/1991 |
| JP | 7-89859 | 4/1995 |
| JP | 2003-513917 | 4/2003 |
| JP | 2008-222603 | 9/2008 |
| JP | 2011-520452 | 7/2011 |
| WO | 01/034138 | 5/2001 |
| WO | 0185931 | 11/2001 |
| WO | 2006034035 | 3/2006 |
| WO | 2009/140568 | 11/2009 |

OTHER PUBLICATIONS

Robertson, N. J. et al., "Methyl-isobutyl amiloride reduces brain Lac/NAA, cell death and microglial activation in a perinatal asphyxia model", Journal of Neurochemistry, vol. 124, 2013, pp. 645-657.

Benos, D. J. et al., "Effect of amiloride and some of its analogues on cation transport in isolated frog skin and thin lipid membranes", Journal of General Physiology, vol. 68, 1976, pp. 43-63.

Durham-Lee, J.C., et al., "Amiloride improves locomotor recovery after spinal cord injury", Journal Neurotrauma, 2011, vol. 28(7), pp. 1319-1326.

Kleyman, T. R. et al., "Amiloride and its analogs as tools in the study of ion transport", Journal Membrane Biol., 1988, vol. 105(1), pp. 1-21.

Aarts, et al. "Treatment of Ischemic Brain Damage by Perturbing NMDA Receptor-PSD-95 Protein Interactions", vol. 298, Science Magazine, pp. 846-850 (2002).

Xiong, et al. "Neuroprotection in Ischemia: Blocking Calcium-Permeable Acid-Sensing Ion Channels", Cell, vol. 118, pp. 687-698 (2004).

Bladin, et al., "Seizures After Stroke—A Prospective Multicenter Study", Arch Neurol., vol. 57, pp. 1617-1622 (2000).

(Continued)

*Primary Examiner* — Anand U Desai

(74) *Attorney, Agent, or Firm* — Ping Wang; Morris, Manning & Martin LLP

(57) ABSTRACT

A composition and method for preventing or reducing the incidence of a transient ischemic attack in a subject at risk for developing a stroke comprises orally administering to the subject a prophylactically effective amount of a pharmaceutical composition comprising an ASIC1a inhibitor capable of penetrating the blood-brain barrier. Preferred ASIC1a inhibitors for use in the disclosed methods include amiloride and amiloride analogs.

18 Claims, 15 Drawing Sheets

Specification includes a Sequence Listing.

(56) References Cited

OTHER PUBLICATIONS

Anderson, et al., “Protection of Focal Cerebral Ischemia by Alkalinization of Systemic pH”, Neurosurgery, vol. 51, pp. 1256-1266 (2002).
Kendal, G.S. et al., “N-methyl-isobutyt-amiloride ameliorates brain injury when commenced before hypoxia ischemia in neonatal mice”, Pediatric Research, vol. 59(2), pp. 227-231 (2006).
Horikawa, N. et al., “The Na+/H+ Exchanger SM-20220 Attenuates Ischemic Injury in in vitro and in vivo Models”, Pharmacology, vol. 63, pp. 76-81 (2001).
Hedge, M. et al., “Amiloride kills malignant glioma cells independent of its inhibition of the sodium-hydrogen exchanger”, The Journal of Pharmacology and Experimental Therapeutics, vol. 310(1), pp. 67-74 (2004).
Ye, Kang, et al., “Neuroprotective Effects of Amiloride”, published Jun. 30, 2008, International Journal of Cerebrovascular Diseases, vol. 16, No. 6, pp. 460-463 (English Abstract).
Santos-Torres, Julio, et al., “Cross-reactivity of acid-sensing ion channel and Na+-H+ exchanger antagonists with nicotinic acetylcholine receptors”, published Nov. 30, 2011, The journal of physiology, vol. 589, No. 21, pp. 5109-5123.
At, Behan, et al., “Acidotoxicity and acid-sensing ion channels contribute to motoneuron degeneration”, published Jul. 11, 2013, Department of Physiology and Medical Physics, et al.
File History of U.S. Appl. No. 15/445,833, filed Feb. 8, 2017.
File History of U.S. Appl. No. 13/972,558, filed May 21, 2013.
International Search Report and Written Opinion of the International Searching Authority of Application No. PCT/US2019/048572 dated Nov. 20, 2019.
Hart, R. G. et al., “Transient ischemic attacks in patients with atrial fibrillation: implications for secondary prevention the European Atrial Fibrillation Trial and Stroke Prevention in Atrial Fibrillation III trial”, Stroke, 2004, vol. 35, pp. 948-951.
Leng, T. D. et al., “Amiloride Analogs as ASIC1a Inhibitors”, CNS Neuroscience & Therapeutics, 2016, vol. 22, pp. 468-476.
International Preliminary Report on Patentability and Written Opinion of International Application No. PCT/US2019/048572 dated Mar. 2, 2021.

* cited by examiner

| VARIANT | IDENTIFIER |
|---|---|
| 50 → FULL LENGTH PcTx1 | (SEQ ID:1) |
| 70 → N-TERMINAL DEL. | (SEQ ID:2) |
| 72 → C-TERMINAL DEL.

CHO 1a, -60 mV

CHO 2a, -60 mV

Structure Activity Relationships (SAR) for hydrophobic amiloride analogs on various channels

COMPOSITION AND METHODS FOR PREVENTING OR REDUCING THE INCIDENCE OF TRANSIENT ISCHEMIC ATTACKS

This application is a continuation application of U.S. patent application Ser. No. 16/114,815, filed Aug. 28, 2018, which is a continuation-in-part application of U.S. patent application Ser. No. 15/445,833, filed on Feb. 28, 2017, now U.S. Pat. No. 10,201,539, which is a continuation application of U.S. patent application Ser. No. 13/972,558, filed Aug. 21, 2013, now U.S. Pat. No. 9,629,838. The entirety of all of the aforementioned applications is incorporated herein by reference.

FIELD

This application relates to the field of neurology and cardiology. In particular, this application related to compositions comprising an ASIC1a inhibitor for preventing or reducing the incidence of TIAs and nerve injuries in a subject.

BACKGROUND

A transient ischemic attack ("TIA" or "mini stroke") is an acute episode of temporary neurologic dysfunction, typically lasting less than an hour (sometimes up to 24 hours). A TIA is caused by a brief interruption of oxygen flow or transient disturbance of blood supply to a tissue, typically due to an obstructing blood clot without infarction. When symptoms persist for a longer time and are accompanied by infarction, the dysfunction is categorized as a stroke.

Whereas the classical definition of TIA included symptoms lasting as long as 24 h, advances in neuroimaging have suggested that many such cases represent minor strokes with resolved symptoms rather than true TIAs. Thus, the American Heart Association and the American Stroke Association (ASA) endorse a tissue-based definition of TIA (i.e., as an episode of focal ischemia rather than acute infarction) rather than a time-based definition.

The most common cause of a TIA is an embolus (blood clot) that occludes an artery in the brain, and to a lesser extent, the spinal cord and retina. Typically, the clots result from an atherosclerotic plaque in one of the two carotid arteries, or from the heart, for example, in patients with atrial fibrillation (AFIB). Symptoms of TIA typically include temporary amaurosis (loss of vision), aphasia (difficulty speaking), hemiparesis (weakness of one side of the body, and/or paresthesia (numbness).

TIAs are often considered as a warning for an approaching stroke. Identification of TIAs is important as the incidence of a subsequent stroke is as high as 11% over the next 7 days and 24-29% over the following 5 years. However, up to 80% of strokes following TIA are preventable. Accordingly, early diagnosis and treatment are critical.

According to current guidelines of the American Stroke Association (ASA), risk factors include nonmodifiable factors (age, sex, race, and significant family history); modifiable factors (body weight, hypertension, unhealthy lipid profile, cerebral microbleeds, cardiovascular diseases, including coronary artery disease, myocardial infarction, peripheral arterial disease, valvular disease, atrial fibrillation, atrial flutter; diabetes mellitus; and lifestyle choices (cigarette smoking, alcohol consumption, illicit drug use, unhealthy diet/poor nutrition, and physical inactivity).

Patients with atrial fibrillation (AFIB) and atrial flutter (AFL) are at a higher risk for developing TIAs and strokes. AFIB affects about 2.3 million people in North America and 4.5 million people in the European Union and is emerging as a growing public health concern because of the aging of the population. AFIB is a condition in which the upper chambers of the heart beat in an uncoordinated and disorganized fashion, resulting in a very irregular and fast rhythm (i.e., an irregularly, irregular heartbeat). When blood is not completely pumped out of the heart's chambers, it can pool and clot. If a blood clot forms in the atria, exits the heart and blocks an artery in the brain, a TIA or stroke results. Consequently, about 15 percent of strokes result from AFIB.

AFL is a common abnormal heart rhythm, similar to AFIB, the most common abnormal heart rhythm. Both conditions are types of supraventricular (above the ventricles) tachycardia (rapid heartbeat). In AFIB, the heart beats fast and in no regular pattern or rhythm. By contrast, in AFL, the upper chambers (atria) of the heart beat abnormally fast, but in a regular pattern, resulting in atrial muscle contractions that are faster than and out of sync with the lower chambers (ventricles). AFL patients exhibit a distinct "sawtooth" pattern on an electrocardiogram (ECG), a test used to diagnose abnormal heart rhythms.

If left untreated, the side effects of AFIB and AFL can be potentially life threatening. With blood pooling in the heart (AFIB) or moving more slowly (AFL), it is more likely to form clots. If the clot is pumped out of the heart, it could travel to the brain, spinal cord, or retina, thereby causing a TIA or stroke.

TIAs and strokes represent different ends of an ischemic continuum from the physiological perspective, but clinical management is similar. In some cases, antiplatelet drugs have been found to be effective in preventing TIAs. Many physicians believe antithrombotic therapy should be initiated as soon as intracranial hemorrhage has been ruled out. For patients with TIA or ischemic stroke of cardiac origin due to atrial fibrillation, vitamin K antagonists (VKAs) are highly effective in preventing recurrent ischemic stroke but have important limitations and are consequently underused. Antiplatelet therapy is less effective than VKAs. The direct thrombin inhibitor, dabigatran etexilate, has shown efficacy over warfarin in a recent trial. Other anticoagulants include oral factor Xa inhibitors, such as rivaroxaban, apixaban, and edoxaban; the parenteral factor Xa inhibitor, idrabiotaparinux, and the VKA, tecarfarin.

Notwithstanding the risks for strokes in patients with AFIB and AFL, however, strokes mainly occur in patients without AFIB or AFL. In view of the foregoing, there is a need for improved medications for preventing TIAs and nerve injuries in patients at risk.

SUMMARY

One aspect of the present application related to a method for preventing or reducing the incidence of a transient ischemic attack in a subject at risk for developing a transient ischemic attack, comprising orally administering to the subject a prophylactically effective amount of a pharmaceutical composition comprising an ASIC1a inhibitor capable of penetrating the blood-brain barrier.

In one embodiment, the ASIC1a inhibitor comprises amiloride, an amiloride analog, or a pharmaceutically acceptable salt or solvate thereof.

In a particular embodiment, the ASIC1a inhibitor comprises amiloride or a pharmaceutically acceptable salt or solvate thereof.

In another embodiment, the ASIC1a inhibitor comprises an amiloride analog or a pharmaceutically acceptable salt or solvate thereof.

In certain embodiments, the amiloride analog is selected from the group consisting of benzamil, bepridil, KB-R7943, phenamil, 5-(N-N-dimethyl) amiloride (DMA), 5-(N,N-hexamethylene) amiloride (HMA), 5-(N-ethyl-N-isopropyl)-amiloride (EIPA), 5-(N-methyl-N-isobutyl) amiloride (MIA), pharmaceutically acceptable salts or solvates thereof, methylated analogs thereof, and combinations thereof.

In other embodiments, the amiloride analog is selected from the group consisting of methylated analogs of benzamil, amiloride analogs containing a ring formed on a guanidine group, amiloride analogs containing an acylguanidino group, and amiloride analogs containing a water solubilizing group formed on a guanidine group, wherein the water solubilizing group is a N,N-dimethyl amino group or a sugar group.

In one embodiment, the pharmaceutical composition is administered daily.

In another embodiment, the pharmaceutical composition is formulated as an extended release formulation.

In preferred embodiments, the subject is at risk for developing TIAs or strokes.

In one embodiment, the subject has recently had heart surgery or has previously had a TIA or stroke.

In another embodiment, subject has an abnormal heart rhythm selected from the group consisting of atrial fibrillation, atrial flutter, ventricular tachycardia, and ventricular fibrillation.

In another embodiment, the subject has acute coronary syndrome, arterial embolism, atherosclerosis, atrial fibrillation, carotid artery disease, cerebral arterial thrombosis, cerebral embolism, coronary arterial thrombosis, coronary heart disease, deep vein thrombosis, kidney embolism, myocardial infarction, peripheral arteriopathy, pulmonary embolism, stroke, thrombophlebitis, thrombosis, transient ischemic attack, unstable angina, valvular heart disease, venous thrombosis, ventricular fibrillation, or a combination thereof.

In one embodiment, the amiloride, amiloride analog or a pharmaceutically acceptable salt or solvate thereof is administered in a dose range of 0.1 mg-10 mg/kg body weight.

In another aspect, the pharmaceutical composition further includes one or more anti-clotting agents, such as antiplatelet agents, anticoagulant agents, anti-arrhythmic agents, or a combination thereof.

In one embodiment, the pharmaceutical composition includes an antiplatelet agent selected from the group consisting of aspirin, clopidogrel, prasugrel, ticagrelor, dipyridamole, and combinations thereof.

In another embodiment, the pharmaceutical composition includes an anticoagulant agent selected from the group consisting of vitamin-K epoxide reductase inhibitors, direct thrombin inhibitors and Factor Xa inhibitors. In a particular embodiment, the anticoagulant agent is selected from the group consisting of heparin, warfarin, dabigatran, apixaban, edoxaban, rivoraxaban, ximelagatran, argatroban, AZD-0837, YM466, betrixaban, edoxaban, tecarfarin, and combinations thereof.

In another embodiment, the pharmaceutical composition includes an anti-arrhythmic agent selected from the group consisting of dronedarone, budiodarone, amiodarone, vernakalant, celivarone, AZD-1305, dofetilide, ibutilide, flecainide, quinidine, sotolol, propafenone, and combinations thereof.

In another aspect, a pharmaceutical composition for reducing nervous system injury, comprises an effective amount of one or more ASIC1a inhibitors selected from the group consisting of amiloride, amiloride analogs, pharmaceutically acceptable salts or solvates thereof, methylated analogs thereof, and combinations thereof; and a pharmaceutically acceptable carrier, wherein the pharmaceutical composition is formulated for oral administration of the one or more ASIC1a inhibitors, wherein the ASIC1a inhibitor(s) are capable of penetrating the blood-brain barrier.

In one embodiment, the ASIC1a inhibitor comprises amiloride or a pharmaceutically acceptable salt or solvate thereof.

In another embodiment, the ASIC1a inhibitor comprises an amiloride analog or a pharmaceutically acceptable salt or solvate thereof. In a particular embodiment, the amiloride analog is selected from the group consisting of benzamil, bepridil, KB-R7943, phenamil, 5-(N-N-dimethyl) amiloride (DMA), 5-(N,N-hexamethylene) amiloride (HMA), 5-(N-ethyl-N-isopropyl)-amiloride (EIPA), 5-(N-methyl-N-isopropyl (MIA), pharmaceutically acceptable salts or solvates thereof, methylated analogs thereof, and combinations thereof.

In another embodiment, the amiloride analog is selected from the group consisting of methylated analogs of benzamil, amiloride analogs containing a ring formed on a guanidine group, amiloride analogs containing an acylguanidino group, and amiloride analogs containing a water solubilizing group formed on a guanidine group, wherein the water solubilizing group is a N,N-dimethyl amino group or a sugar group.

In another embodiment, the pharmaceutical composition comprises an extended release formulation for delivery of the one or more ASIC1a inhibitors.

In other embodiments, the pharmaceutical composition further comprises one or more antiplatelet agents selected from the group consisting of aspirin, clopidogrel, prasugrel, and ticagrelor, and combinations thereof.

In another embodiment, the pharmaceutical composition further comprises one or more anticoagulant agents selected from the group consisting of vitamin-K epoxide reductase inhibitors, direct thrombin inhibitors and Factor Xa inhibitors. In certain embodiments, the one or more anticoagulant agents are selected from the group consisting of apixaban, argatroban, AZD-0837, betrixaban, dabigatran, edoxaban, heparin, rivoraxaban, tecarfarin, warfarin, ximelagatran, YM466, and combinations thereof.

In another embodiment, the pharmaceutical composition further comprises one or more anti-arrhythmic agents. In certain embodiments, the more anti-arrhythmic agents are selected from the group consisting of amiodarone, AZD-1305, budiodarone, celivarone, dofetilide, dronedarone, flecainide, ibutilide, propafenone, quinidine, sotolol, vernakalant, and combinations thereof.

DETAILED DESCRIPTION

Definitions

Figure 1:
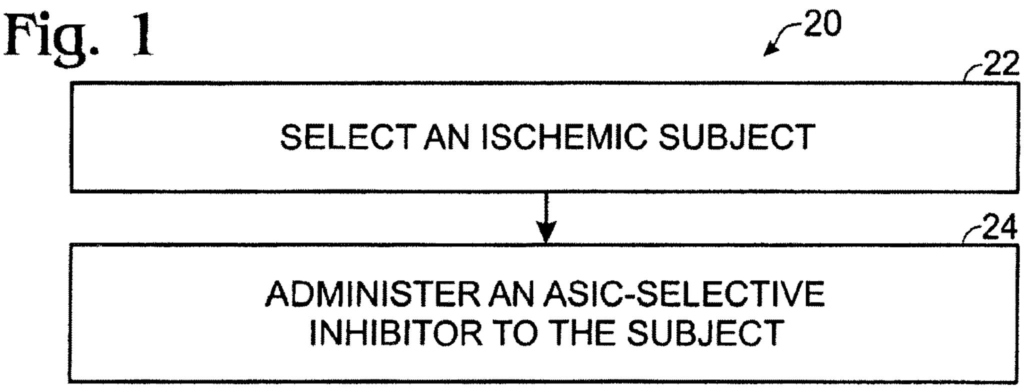
FIG. 1 is a view of a flowchart illustrating an exemplary method of reducing neuroinjury in an ischemic subject.

As used herein, the term "nervous system" includes both the central nervous system and the peripheral nervous system.

The term "amiloride analog" includes structural analogs of amiloride, functional analogs of amiloride, or a combination thereof.

The term "central nervous system" or "CNS" includes all cells and tissue of the brain and spinal cord of a vertebrate.

The term "peripheral nervous system" refers to all cells and tissue of the portion of the nervous system outside the brain and spinal cord, such as the motor neurons that mediate voluntary movement, the autonomic nervous system that includes the sympathetic nervous system and the parasympathetic nervous system and regulates involuntary functions, and the enteric nervous system that controls the gastrointestinal system. Thus, the term "nervous system" includes, but is not limited to, neuronal cells, glial cells, astrocytes, cells in the cerebrospinal fluid (CSF), cells in the interstitial spaces, cells in the protective coverings of the spinal cord, epidural cells (i.e., cells outside of the dura mater), cells in non-neural tissues adjacent to or in contact with or innervated by neural tissue, cells in the epineurium, perineurium, endoneurium, funiculi, fasciculi, and the like.

As used herein, the term "patient" encompasses all mammalian species.

As used herein, the terms "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, the term "risk reduction" covers therapies that lower the incidence of development of a clinical disease state. As such, primary and secondary prevention therapies are examples of risk reduction.

As used herein, the phrase "prophylactically effective amount" is intended to include an amount of an ASIC la inhibitor and/or an anti-clotting agent described in the present application that is effective to prevent or reduce the incidence of a TIA. When applied to a combination, the term refers to combined amounts of the active ingredients that result in a preventive effect, whether administered in combination, serially, or simultaneously.

As used herein, the phrase "therapeutically effective amount" is intended to include an amount of an ASIC1a inhibitor and/or an anti-clotting agent described in the present application that is effective to treat a subject that has had a TIA and/or effective to prevent and/or reduce the incidence of stroke. When applied to a combination, the term refers to combined amounts of the active ingredients that result in the preventive or therapeutic effect, whether administered in combination, serially, or simultaneously.

As used herein, the term "thrombosis" refers to formation or presence of a thrombus (pl. thrombi): clotting within a blood vessel that may cause ischemia or infarction of tissues supplied by the vessel.

The term "embolism", as used herein, refers to sudden blocking of an artery by a clot or foreign material that has been brought to its site of lodgment by the blood current.

The term "thromboembolism", as used herein, refers to obstruction of a blood vessel with thrombotic material carried by the blood stream from the site of origin to plug another vessel.

The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, valvular heart disease, ventricular fibrillation, and thrombosis resulting from medical implants, devices, or procedures in which blood is exposed to an artificial surface that promotes thrombosis.

The present application provides methods and compositions for preventing, treating and/or reducing the risk of transient ischemic attacks (TIAs) or ischemic stroke.

One aspect of the present application related to a method for preventing or reducing the incidence of a TIA in a subject at risk for developing a TIA, comprising orally administering to the subject a prophylactically effective amount of a pharmaceutical composition comprising an ASIC1a inhibitor capable of penetrating the blood-brain barrier.

Asic Inhibitors, Amiloride and Amiloride Analogs

The term "ASIC1a", as used herein, refers to an ASIC1a protein or channel from any species. The expression "ASIC1a inhibitor" refers to a product which inhibits acid sensing ion channel 1a (ASIC1a). For example, an exemplary human ASIC1a protein/channel is described in Waldmann, R., et al. 1997, Nature 386, pp. 173-177.

The ASIC1a inhibitor may be selective within the ASIC family. Selective inhibition of ASIC1a, as used herein, is inhibition that is substantially stronger on ASIC1a than on another ASIC family member(s) when compared (for example, in cultured cells) after exposure of each to the same (sub-maximal) concentration(s) of an inhibitor. The inhibitor may inhibit ASIC1a selectively relative to at least one other ASIC family member (ASIC1b, ASIC2a, ASIC2b, ASIC3, ASIC 4, etc.) and/or selectively relative to every other ASIC family member. The strength of inhibition for a selective inhibitor may be described by an inhibitor concentration at which inhibition occurs (e.g., an $IC_{50}$ (inhibitor concentration that produces 50% of maximal inhibition) or a $K_i$ value (inhibition constant or dissociation constant)) relative to different ASIC family members. An ASIC1a-selective inhibitor may inhibit ASIC1a activity at a concentration that is at least about two-, four-, or ten-fold lower (one-half, one-fourth, or one-tenth the concentration or lower) than for inhibition of at least one other or of every other ASIC family member. Accordingly, an ASIC1a-selective inhibitor may have an $IC_{50}$ and/or $K_i$ for ASIC1a inhibition that is at least about two-, four-, ten-, or twenty-fold lower (one-half, one-fourth, one-tenth, one-twentieth or less) than for inhibition of at least one other ASIC family member and/or for inhibition of every other ASIC family member.

Accordingly, an ASIC1a -specific inhibitor may have an $IC_{50}$ and/or $K_i$ for ASIC1a relative to every other member of the ASIC family that is at least about twenty-fold lower (five percent or less), such that, for example, inhibition of other ASIC family members is at least substantially (or completely) undetectable. In some embodiments, the ASIC1a-selective inhibitor has increased potency to homomeric ASIC1a channel and increased aqueous solubility comparing to any commercially available amiloride-related ASIC1a inhibitor.

In one embodiment, the ASIC1a inhibitor is selected from the group consisting of amiloride, amiloride analogs, and pharmaceutically acceptable salts or solvates thereof.

In one embodiment, the ASIC1a inhibitor is amiloride or a pharmaceutically acceptable salt or solvate thereof. Amiloride, a guanidinium group containing pyrazine derivative, has been used for the treatment of mild hypertension with little reported side effect. Amiloride works by directly blocking the epithelial sodium channel (ENaC) thereby inhibiting sodium reabsorption in the late distal convoluted tubules, connecting tubules, and collecting ducts in the kidneys. This promotes the loss of sodium and water from the body, but without depleting potassium. As used herein, the term "amiloride" refers to both amiloride and salts of amiloride, such as amiloride hydrochloride.

In another embodiment, the ASIC1a inhibitor is an amiloride analog or a pharmaceutically acceptable salt or solvate thereof. Amiloride analogs, as used herein, refer to chemical compounds having biological activities similar to those of amiloride but with a slightly altered chemical structure.

In some embodiments, the amiloride analogs do not to block the human $Na^+/Ca^{2+}$ ion exchanger. In other embodiments, the amiloride analog is a weak inhibitor of the $Na^+/Ca^{2+}$ ion exchanger and helps to maintain low levels of intracellular $Ca^{2+}$. In other embodiments, the amiloride analog is a very weak inhibitor of the $Na^+/Ca^{2+}$ ion exchanger with an $IC_{50}$ of 1.1 mM or less. In other embodiments, the amiloride analogs do not block the ASIC2a and/or ASIC3 channels. In one embodiment, the amiloride analog has increased selectivity for ASIC1a over the ASIC3 channel and/or ASIC2 channel.

Exemplary amiloride analogs for use in the present application include, but are not limited to benzamil, bepridil, KB-R7943, phenamil, 5-(N-N-dimethyl) amiloride (DMA), 5-(N,N-hexamethylene) amiloride (HMA), 5-(N-ethyl-N-isopropyl)-amiloride (EIPA), 5 -(N-methyl-N-isopropyl (MIA), pharmaceutically acceptable salts or solvates thereof, methylated analogs thereof, and combinations thereof.

Figure 21:
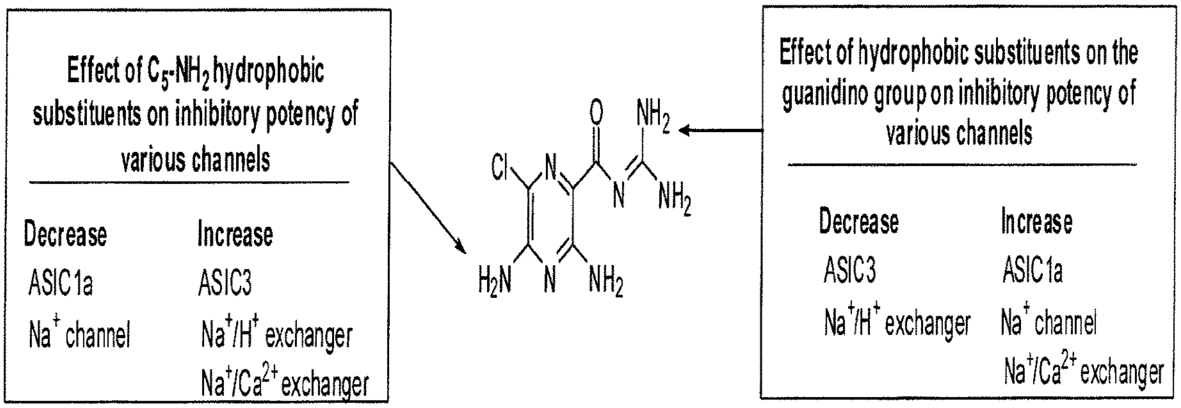
FIG. 21 shows structure activity relationship (SAR) for hydrophobic amiloride analogs on various channels.

In some embodiments, the amiloride analog has a hydrophobic substituent at the $C_5$—$NH_2$ position and/or on the guanidino group, as shown in FIG. 21 below. In other embodiments, the amiloride analog is selected from the group consisting of methylated analogs of benzamil, amiloride analogs containing a ring formed on a guanidine group, amiloride analogs containing an acylguanidino group, and amiloride analogs containing a water solubilizing group formed on a guanidine group, wherein the water solubilizing group is a N,N-dimethyl amino group or a sugar group.

Any suitable ASIC inhibitor or combination of inhibitors may be used. For example, a subject may be treated with an ASIC1a-selective inhibitor and a nonselective ASIC inhibitor, or with an ASIC1a-selective inhibitor and an inhibitor to a non-ASIC channel protein, such as a non-ASIC calcium channel. In some examples, a subject may be treated with an ASIC1a-selective inhibitor and an inhibitor of NMDA receptors, such as a glutamate antagonist.

In other embodiments, the ASIC1a inhibitor is a peptide. The peptide may have any suitable number of amino acid residues, generally at least about ten, but less than a thousand residues, and more typically less than a hundred residues. In some embodiments, the peptide may have a cystine knot motif. A cystine knot, as used herein, generally includes an arrangement of six or more cysteines. A peptide with these cysteines may create a "knot" including (1) a ring formed by two disulfide bonds and their connecting backbone segments, and (2) a third disulfide bond that threads through the ring. In some examples, the peptide may be a conotoxin from an arachnid and/or cone snail species. For example, the peptide may be PcTx1 (psalmotoxin 1), a toxin from a tarantula (*Psalmopoeus cambridgei* (Pc)). In other embodiments, the peptide may be one of four disulfide-rich spider venom peptides from the Australian funnel-web spider *Hadronyche infensa* (i.e., Hi1a, Hi1b, Hi1c, Hi1d), which contains two tandem PcTx1-like sequences joined by a short linker.

In some examples, the peptide may be structurally related to PcTx1, such that the peptide and PcTx1 differ by at least one deletion, insertion, and/or substitution of one or more amino acids. For example, the peptide may have at least about 25% or at least about 50% sequence identity, and/or at least about 25% or at least about 50% sequence similarity with PcTx1 (see below). Further aspects of peptides that may be suitable as inhibitors are described below in Example 3.

Methods of alignment of amino acid sequences for comparison and generation of identity and similarity scores are well known in the art. Exemplary alignment methods that may be suitable include (Best Fit) of Smith and Waterman, a homology alignment algorithm (GAP) of Needleman and Wunsch, a similarity method (Tfasta and Fasta) of Pearson and Lipman, and/or the like. Computer algorithms of these and other approaches that may be suitable include, but are not limited to: CLUSTAL, GAP, BESTFIT, BLASTP, FASTA, and TFASTA.

As used herein, "sequence identity" or "identity" in the context of two peptides relates to the percentage of residues in the corresponding peptide sequences that are the same when aligned for maximum correspondence. In some examples, peptide residue positions that are not identical may differ by conservative amino acid substitutions, where amino acid residues are substituted for other amino acid residues with similar chemical properties (e.g., charge or hydrophobicity) and therefore are expected to produce a smaller (or no) effect on the functional properties of the molecule. Where sequences differ in conservative substitutions, the percent sequence identity may be adjusted upwards, to give a "similarity" of the sequences, which corrects for the conservative nature of the substitutions. For example, each conservative substitution may be scored as a partial rather than a full mismatch, thereby correcting the percentage sequence identity to provide a similarity score. The scoring of conservative substitutions to obtain similarity scores is well known in the art and may be calculated by any suitable approach, for example, according to the algorithm of Meyers and Miller, Computer Applic. Biol Sci., 4: 11-17 (1988), e.g., as implemented in the program PC/GENE (Intelligenetics, Mountain View, Calif., USA).

Anti-Clotting Agents

In another aspect, the pharmaceutical composition comprising one or more ASIC1a inhibitors further includes one or more anti-clotting agents. Anti-clotting agents for use in the present application include antiplatelet agents, anticoagulant agents, anti-arrhythmic agents, or a combination thereof. Use of these anti-clotting agents may further increase the prophylactic and/or therapeutic efficacy of the ASIC1a inhibitor(s) administered to a subject in need thereof, either combinatorially or synergistically.

In one embodiment, the pharmaceutical composition further includes one or more antiplatelet agents. Exemplary antiplatelet agents include, but are not limited to COX inhibitors, adenosine diphosphate (ADP) receptor inhibitors, phosphodiesterase inhibitors, Glycoprotein IIb/IIIa inhibitors, adenosine reuptake inhibitors, thromboxane inhibitors, and combinations thereof. Some of the antiplatelet agents have multiple modes of action as reflected in the lists below.

COX inhibitors include acetylsalicylic acid (e.g., Aspirin) and triflusal (e.g., Disgren, Grendis, Aflen and Triflux), which irreversibly inhibit the COX-1 enzyme, prostaglandin-endoperoxide synthase-1 (i.e., COX-1 or PTGS1) and modify the enzymatic activity of the COX-2 enzyme (i.e., COX-2 or PTGS2), as well reversible COX-2 inhibitors targeting COX-2/PTGS2, such as celecoxib (e.g., Celebrex).

Adenosine diphosphate (ADP) receptor inhibitors for use in the present application include reversible or irreversible anatagonists of $P2Y_{12}$ ADP receptors. Exemplary ADP receptor inhibitors include thienopyridines, such as the irreversible $P2Y_{12}$ inhibitors, prasugrel, clopidogrel (e.g., Plavix), and reversible $P2PY_{12}$ inhibitors, such as ticagrelor (e.g., Brilinta).

Phosphodiesterase inhibitors for use in the present application include, but are not limited to dipyridamole (e.g., Persantine), cilostazol (e.g., Pletal), triflusal (e.g., Disgren, Grendis, Aflen and Triflux), and vorapaxar (e.g., Zontivity).

Glycoprotein IIb/IIIa inhibitors for use in the present application include, but are not limited to abciximab (e.g., ReoPro), eptifibatide (e.g., Integrilin), ifetroban, iloprost, isocarbacyclin methyl ester, itazigrel, lamifiban, lifarizine, molsidomine, nifedipine, orbofiban, oxagrelate, roxifiban, and tirofiban (Aggrastat).

Adenosine reuptake inhibitors for use in the present application include, but are not limited to acadesine, acetate, barbiturates, benzodiazepines, calcium channel inhibitors, carbamazepine, carisoprodol, cilostazol (Pletal), cyclobenzaprine, dilazep, estradiol, ethanol, flumazenil, hexobendine, hydroxyzine, indomethacin, inosine, KF24345, meprobamate, nitrobenzylthioguanosine, nitrobenzylthioinosine, papaverine, pentoxifylline, phenothiazines, phenytoin, progesterone, propentofylline, propofol, puromycin, R75231, RE 102 BS, soluflazine, toyocamycin, tracazolate, and tricyclic antidepressants.

Thromboxane inhibitors for use in the present application inhibit the synthesis of thromboxane and/or inhibit the target effect of thromboxane. Exemplary thromboxane inhibitors include, but are not limited to acetylsalicylic acid (e.g., Aspirin), dipyridamole, ifetroban, naproxen, picotamide, ridogrel, sulotroban, terutroban, ticlopidine, trapidil, triclopidine, trifenagrel, trifusal (e.g., Disgren, Grendis, Aflen and Triflux), and trilinolein.

In another embodiment, the pharmaceutical composition further includes one or more anticoagulant agents. In a particular embodiment, the anticoagulant agent is a vitamin-K epoxide reductase inhibitor. In other embodiments, the anticoagulant agent is a direct Factor Xa inhibitor, an indirect Factor Xa inhibitor, a direct thrombin inhibitor, or an indirect thrombin inhibitor (which are collectively known as direct oral anticoagulants (DOACs) or non-VKA oral anticoagulants). Vitamin K-epoxide reductase inhibitors for use in combination with the ASIC1a inhibitors of the present application include 4-hydroxycoumarin derivatives and 1,3-indandione derivatives. Exemplary vitamin K epoxide reductase inhibitors include, but are not limited to acenocoumarol (e.g., Sintrom and Sinthrome), anisindione, clorindione, coumarin, coumadin (e.g., warfarin), dicumarol and its derivatives (e.g., bis-hydroxycoumarin, bishydroxycoumarin, dicoumarin, dicoumarol), disulfiram, ethyl biscoumacetate, N-ethylmaleimide, fluindione, phenindione (e.g., Dindevan), phenprocoumon (e.g., Marcoumar, Marcumar and Falithrom), 1-N-methyl-5-thiotetrazole, 5,5'-dithiobis(1-methyltetrazole), pharmaceutically acceptable salts and solvates thereof, and combinations thereof.

Non-VKA oral anticoagulants (NOACs) for use in the present application include direct factor Xa inhibitors, such as apixaban (e.g., Eliquis), edoxaban (e.g., Savaysa, Lixiana), rivaroxaban (e.g., Xarelto), betrixaban (e.g., Bevyxxa), and YM466; direct thrombin inhibitors (or factor IIa inhibitors), such as AZD-0837, dabigatran (e.g., Pradaxa, Pradax, and Prazaxa), ximelagatran (e.g., Exanta), and melagatran, the active form of ximelagatran; indirect factor Xa inhibitors, such as fondaparinux (e.g., Arixtra), ultralow molecular weight heparin (ULMWH); indirect thrombin inhibitors, such as heparin, antithrombin, heparin in combination with antithrombin, enoxaparin (e.g., Lovenox), low molecular weight heparin (LMWH), dalteparin sodium (e.g., Fragmin), batroxobin, and hementin; including salts and solvates thereof, and combinations thereof.

In another embodiment, the pharmaceutical composition for use in the present application further includes one or more anti-arrhythmic agents. Exemplary anti-arrhythmic agents include amiodarone, AZD-1305, budiodarone, celivarone, dofetilide, dronedarone, ibutilide, flecainide, propafenone, quinidine, sotolol, vernakalant, and combinations thereof.

Any single, plurality, or combination of anticoagulants, salts thereof, solvates thereof, and derivatives thereof, may be used for modulating anticoagulant function, including other anticoagulants not mentioned here without departing from the present application.

Administration of Inhibitors

Administration of the ASIC1a inhibitors and/or the additional anti-clotting agents may be performed once or a plurality of times, and at any suitable time relative to TIA diagnosis, to alleviate the risk of an additional TIA and/or stroke. Accordingly, administration may be performed before (e.g., prophylactically) or after a TIA has been detected, after a minor ischemic episode, during chronic ischemia, after a full stroke, and/or the like.

In preferred embodiments, the ASIC1a inhibitors and/or anti-clotting agents of the present application are orally administered in a prophylactically effective amount (or simply "an effective amount"). A prophylactically effective amount or an effective amount of an inhibitor or agent, as used herein, is any amount of the inhibitor or agent that, when administered to subjects, reduces, in a significant number of the subjects, the degree, incidence, and/or extent of transient ischemic attacks (TIAs) in the subject. Accordingly, a prophylactically effective amount may be determined, for example, in clinical studies in which various amounts of the inhibitor are administered to test subjects (and, generally, compared to a control group of subjects). Alternatively, one or more of the anti-clotting agents may be administered in a therapeutically effective amounts and/or may be administered intravenously, intramuscularly, intrathecally or intracerebroventricularly.

In some embodiments, the ASIC1a inhibitor and/or anti-clotting agents are formulated, individually or in combination, for daily administration in one or more doses in the range of 0.01-30 mg/kg body weight, 0.01-10 mg/kg body weight, 0.01-3 mg/kg body weight, 0.01-1 mg/kg body weight, 0.01-0.3 mg/kg body weight, 0.01-0.1 mg/kg body weight, 0.01-0.03 mg/kg body weight, 0.03-30 mg/kg body weight, 0.03-10 mg/kg body weight, 0.03-3 mg/kg body weight, 0.03-1 mg/kg body weight, 0.03-0.3 mg/kg body weight, 0.03-0.1 mg/kg body weight, 0.1-30 mg/kg body weight, 0.1-10 mg/kg body weight, 0.1-3 mg/kg body weight, 0.1-1 mg/kg body weight, 0.1-0.3 mg/kg body weight, 0.3-30 mg/kg body weight, 0.3-10 mg/kg body weight, 0.3-3 mg/kg body weight, 0.3-1 mg/kg body weight, 1-30 mg/kg body weight, 1-10 mg/kg body weight, 1-3 mg/kg body weight, 3-30 mg/kg body weight, 3-10 mg/kg body weight or 10-30 mg/kg body weight.

In other embodiments, the ASIC1a inhibitor and/or other anti-clotting agent(s) are formulated, individually or in combination, in one or more doses in the range of 0.1-1000 mg/dose, 0.1-300 mg/dose, 0.1-100 mg/dose, 0.1-30 mg/dose, 0.1-10 mg/dose, 0.1-3 mg/dose, 0.1-1 mg/dose, 0.1-0.3 mg/dose, 0.3-1000 mg/dose, 0.3-300 mg/dose, 0.3-100 mg/dose, 0.3-30 mg/dose, 0.3-10 mg/dose, 0.3-3 mg/dose, 0.3-1 mg/dose, 1-1000 mg/dose, 1-300 mg/dose, 1-100 mg/dose, 1-30 mg/dose, 1-10 mg/dose, 1-3 mg/dose, 3-1000 mg/dose, 3-300 mg/dose, 3-100 mg/dose, 3-30 mg/dose, 3-10 mg/dose, 10-1000 mg/dose, 10-300 mg/dose, 10-100 mg/dose, 10-30 mg/dose, 30-1000 mg/dose, 30-300 mg/dose, 30-100 mg/dose, 100-1000 mg/dose, 100-300 mg/dose, or 300-1000 mg/dose.

The inhibitor(s) may be administered in any suitable form and in any suitable composition to subjects. In some examples, the inhibitors may be configured as a pharmaceutically acceptable salt or solvate. The composition(s) may be formulated to include, for example, a fluid carrier/solvent (a vehicle), a preservative, one or more excipients, a coloring agent, a flavoring agent, a salt(s), an anti-foaming agent, and/or the like. The inhibitor(s) may be present at a concentration in the vehicle that provides a prophylactically or therapeutically effective amount of the inhibitor(s) for prevention or treatment of TIAs when administered to a subject at risk for developing a TIA or stroke.

In some embodiments, amiloride analogs with higher water solubility or lipid solubility are used. For example, the amiloride analog may contain a water solubilizing group, such as an N,N-dimethyl amino group or a sugar, at the guanidino group to improve water solubility (formula 13-16, FIG. 24). In some embodiments, the amiloride analog has a water solubility of 5 mM, 10 mM, 20 mM, 30 mM, 40 mM, 50 mM, 60 mM, 70 mM, 80 mM, 90 mM, 100 mM or higher. In other embodiments, the amiloride analog has a solubility that allows for a 10 mg, 25 mg, 50 mg, 100 mg, 150 mg, 200 mg, 250 mg, 300 mg, 400 mg, or 500 mg dose for oral administration.

Generally, the pharmaceutical compositions of the present application include one or more pharmaceutically acceptable carrier(s). As used herein, a "pharmaceutically acceptable carrier" includes any and all solvents, dispersion media, coatings, antibacterial and antifungal agents, isotonic and absorption delaying agents, sweeteners and the like. The pharmaceutically acceptable carriers may be prepared from a wide range of materials including, but not limited to flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the prophylactic or therapeutic compositions is contemplated. Optionally, the amiloride and/or an amiloride analog may be combined with other active ingredients, which are not contraindicated by the ASIC1a inhibitor(s), including amiloride and/or its analog(s), and which further increase the prophylactic and/or therapeutic efficacy of the ASIC1a inhibitor(s).

In preferred embodiments, the pharmaceutical composition is formulated for oral administration. In particular embodiments, the pharmaceutical composition is provided in a dry form, and is formulated into a tablet or capsule form. Tablets may be formulated in accordance with conventional procedures employing solid carriers well-known in the art. Hard and soft capsules employed in the present invention can be made from any pharmaceutically acceptable material, such as gelatin or cellulosic derivatives.

In other embodiments, the pharmaceutical composition is formulated for intravenous injection, intramuscular injection, intrathecal injection or intracerebroventricular injection. Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable compositions are sterile and are fluid to the extent that easy syringability exists. The injectable composition is preferably stable under the conditions of manufacture and storage and preserved against the contaminating action of microorganisms such as bacteria and fungi.

The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the requited particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active agent(s) in the required amount(s) in an appropriate solvent, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active, ingredient plus any additional desired ingredient from a previously sterile-filtered solution thereof.

In certain embodiments, the pharmaceutical composition is formulated for controlled release of the ASIC1a inhibitor and/or anti-clotting agents in the composition. A controlled release formulation may be designed for immediate release, extended-release, delayed-release or a combination thereof. Extended-release, also known as sustained-release, time-release or timed-release, controlled-release (CR), modified release (MR), or continuous-release (CR or Contin), provides a mechanism for the slow release over time of one or more active agents, typically in an oral formulation comprising tablets or capsules to dissolve slowly and release the active ingredient over time. The advantages of sustained-release tablets or capsules are that they can often be taken less frequently than instant-release formulations of the same drug, and that they keep steadier levels of the drug in the bloodstream, thus extending the duration of the drug action.

In one embodiment, the pharmaceutical composition is formulated for extended release by embedding the active ingredient in a matrix of insoluble substance(s) such as acrylics or chitin. An extended release form is designed to release the active ingredient at a predetermined rate by maintaining a constant drug level for a specific period of time.

In another embodiment, the pharmaceutical composition is formulated for delayed-release, such that the active ingredient(s) is not immediately released upon administration. A non-limiting example of a delayed release vehicle is an enteric coated oral medication that dissolves in the intestines rather than the stomach.

In other embodiments, the pharmaceutical composition is formulated for immediate release of a portion of the active ingredient(s), followed by extended-release of the remainder of the active ingredient(s). In one embodiment, the pharmaceutical composition is formulated as a powder that can be ingested for rapid release of the active ingredient. In another embodiment, the pharmaceutical composition is formulated into a liquid, gel, liquid suspension or emulsion form. Said liquid, gel, suspension or emulsion may be ingested by the subject in naked form or contained within a capsule.

In yet another embodiment, the pharmaceutical composition may be provided as a skin or transdermal patch for the topical administration of controlled and/or sustained quantities of the active ingredient.

Methods for Preventing or Treating Disease

One aspect of the present application relates to a method for preventing or treating a transient ischemic attack (TIA) in a subject. In one embodiment, the method includes orally administering to the subject a therapeutically effective amount of a pharmaceutical composition comprising an ASIC1a inhibitor as described above. In other embodiments, the pharmaceutical composition is administered intravenously, intramuscularly, intrathecally or intracerebroventricularly.

The method and pharmaceutical composition of the present application can be used in any subject at risk for developing TIAs and/or stroke.

Risk factors include nonmodifiable factors (age, sex, race, and significant family history); modifiable factors (body weight, hypertension, unhealthy lipid profile, cerebral microbleeds, cardiovascular diseases, including coronary artery disease, myocardial infarction, peripheral arterial disease, valvular disease, atrial fibrillation, atrial flutter; diabetes mellitus; and lifestyle choices (cigarette smoking, alcohol consumption, illicit drug use, unhealthy diet/poor nutrition, and physical inactivity).

In one embodiment, the subject is at risk for developing a TIA or stroke.

In another embodiment, the subject has recently had heart surgery or has been previously diagnosed as having had a TIA or stroke.

In another embodiment, subject has an abnormal heart rhythm selected from the group consisting of atrial fibrillation, atrial flutter, ventricular tachycardia, and ventricular fibrillation.

In another embodiment, the compositions of the present application may be used in a method for treatment of a thromboembolic disorder selected from the group consisting of acute coronary syndrome, arterial embolism, atherosclerosis, atrial fibrillation, carotid artery disease, cerebral arterial thrombosis, cerebral embolism, coronary arterial thrombosis, coronary heart disease, deep vein thrombosis, kidney embolism, myocardial infarction, peripheral arteriopathy, pulmonary embolism, stroke, thrombophlebitis, thrombosis, transient ischemic attack, unstable angina, valvular heart disease, ventricular fibrillation, and venous thrombosis or combination thereof.

In another embodiment, the subject has diabetes or sickle cell disease.

The subject may be an animal subject or a human subject. The term "animal", as used herein, refers to any animal that is not human. Exemplary animals that may be suitable include any animal with a bloodstream, such as rodents (mice, rats, etc.), dogs, cats, birds, sheep, goats, non-human primates, etc. The animal may be treated for its own sake, e.g., for veterinary purposes (such as treatment of a pet). Alternatively, the animal may provide an animal model of nerve injury, such as ischemia, to facilitate testing drug candidates for human use, such as to determine the candidates' potency, window of effectiveness, side effects, etc.

In another aspect, the present application provides a method for preventing or treating a nerve injury in a subject. In one embodiment, the method includes orally administering to the subject a therapeutically effective amount of a pharmaceutical composition comprising an ASIC1a inhibitor as described above. In other embodiments, the pharmaceutical composition is administered intravenously, intramuscularly, intrathecally or intracerebroventricularly.

In some embodiments, the subject has ischemia, an ischemia-related condition, a history of ischemia, and/or a significant chance of developing ischemia after prophylactic or therapeutic treatment has begun and during a time period in which prevention or treatment is still effective.

Subjects for prevention and/or treatment may be selected by any suitable criteria. Exemplary criteria may include any detectable symptoms of ischemia, a history of ischemia, an event that increases the risk of (or induces) ischemia (such as a surgical procedure, trauma, administration of a medication, etc.), and/or the like. A history of ischemia may involve one or more prior ischemic episodes. In some examples, a subject selected for treatment may have had an onset of ischemia that occurred at least about one, two, or three hours before treatment begins, or a plurality of ischemic episodes (such as transient ischemic attacks) that occurred less than about one day, twelve hours, or six hours prior to initiation of treatment.

As used herein, the term "nerve injury" means an acute or chronic injury to or adverse condition of a nervous system tissue or cell resulting from physical transaction or trauma, contusion or compression or surgical lesion, vascular pharmacologic insults including hemorrhagic or ischemic damage, or from neurodegenerative or any other neurological disease, or any other factor causing the injury to or adverse condition of the nervous system tissue or cell. In some embodiments, the nerve injury is caused by cognitive disorders, psychotic disorders, neurotransmitter-mediated disorders or neuronal disorders. Nerve injury includes injuries to the nervous system (i.e., nervous system injuries) and brain injury.

As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction or Lyme disease associated cognitive dysfunction. In some embodiments, the cognitive disorders are degenerative cognitive disorders. Examples of degenerative cognitive disorders include Alzheimer's Disease, Huntington's Disease, Parkinson's Disease, amyotrophic lateral sclerosis (ALS), autism, mild cognitive impairment (MCI), stroke, traumatic brain injury (TBI), age-associated memory impairment (AAMI) and epilepsy.

As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety, depression and chronic pain.

As used herein, the term "neurotransmitter-mediated disorders" refers to and intends diseases or conditions that are believed to involve or be associated with or do involve or are associated with abnormal levels of neurotransmitters such as histamine, glutamate, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited, to Alzheimer's disease, Parkinson's Disease, autism, Guillain-Barre syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases.

As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barre syndrome, multiple sclerosis, diabetic neuropathy, fibromyalgia, neuropathy associated with spinal cord injury, schizophrenia, bipolar disorder, psychosis, anxiety or depression, and chronic pain.

In some embodiments, the nerve injuries or nervous system injuries are caused by a change in the ion flux into neurons or a nervous system tissue. As used herein, the term “nervous system tissue” refers to animal tissue comprising nerve cells, neuropils, glia, neural inflammatory cells, and endothelial cells in contact with “nervous system tissue”. “Nerve cells” may be any type of nerve cell known to those of skill in the art including, but not limited to neurons. As used herein, the term “neuron” represents a cell of ectodermal embryonic origin derived from any part of the nervous system of an animal. Neurons express well-characterized neuron-specific markers, including neurofilament proteins, NeuN (Neuronal Nuclei marker), MAP2, and class III tubulin. Included as neurons are, for example, hippocampal, cortical, midbrain dopaminergic, spinal motor, sensory, enteric, sympathetic, parasympathetic, septal cholinergic, central nervous system and cerebellar neurons. “Glial cells” useful in the present invention include, but are not limited to astrocytes, Schwan cells, and oligodendrocytes. “Neural inflammatory cells” useful in the present application include, but are not limited to cells of myeloid origin including macrophages and microglia.

In some embodiments, the pharmaceutical compositions and methods of the present application relate to reducing nerve injuries caused by ischemia or an ischemia-related condition. Ischemia, as used herein, is a reduced blood flow to an organ(s) and/or tissue(s). The reduced blood flow may be caused by many mechanisms, including but are not limited to, a partial or complete blockage (an obstruction), a narrowing (a constriction), and/or a leak/rupture, of one or more blood vessels that supply blood to the organ(s) and/or tissue(s). Ischemia may be created by thrombosis, an embolism, atherosclerosis, hypertension, hemorrhage, an aneurysm, surgery, trauma, medication, and the like. The reduced blood flow thus may be chronic, transient, acute or sporadic.

An ischemia-related condition may be any consequence of ischemia. The consequence may be substantially concurrent with the onset ischemia (e.g., a direct effect of the ischemia) and/or may occur substantially after ischemia onset and/or even after the ischemia is over (e.g., an indirect, downstream effect of the ischemia, such reperfusion of tissue when ischemia ends). Exemplary ischemia-related conditions may include any combination of the symptoms (and/or conditions) listed above. Alternatively, or in addition, the symptoms may include local and/or systemic acidosis (pH decrease), hypoxia (oxygen decrease), free radical generation, and/or the like.

In some embodiments, the ischemia-related condition is stroke. Stroke, as used herein, is brain ischemia produced by a reduced blood supply to a part (or all) of the brain. Symptoms produced by stroke may be sudden (such as loss of consciousness) or may have a gradual onset over hours or days. Furthermore, the stroke may be a major ischemic attack (a full stroke) or a more minor, transient ischemic attack, among others. Symptoms produced by stroke may include, for example, hemiparesis, hemiplegia, one-sided numbness, one-sided weakness, one-sided paralysis, temporary limb weakness, limb tingling, confusion, trouble speaking, trouble understanding speech, trouble seeing in one or both eyes, dim vision, loss of vision, trouble walking, dizziness, a tendency to fall, loss of coordination, sudden severe headache, noisy breathing, and/or loss of consciousness. Alternatively, or in addition, the symptoms may be detectable more readily or only via tests and/or instruments, for example, an ischemia blood test (e.g., to test for altered albumin, particular protein isoforms, damaged proteins, etc.), an electrocardiogram, an electroencephalogram, an exercise stress test, brain CT or MRI scanning and/or the like.

Acid-base balance is important for biological systems. Normal brain function depends on the complete oxidation of glucose, with the end product of $CO_2$ and $H_2O$ for its energy requirements. During ischemia, increased anaerobic glycolysis, due to the lack of oxygen supply, leads to lactic acid accumulation. Accumulation of lactic acid, along with increased $H^+$ release from ATP hydrolysis, causes decreases in tissue pH. Extracellular pH ($pH_o$) typically falls to 6.5 during ischemia, and it can fall below 6.0 during severe ischemia or under hyperglycemic conditions.

Any organ or tissue may experience a reduced blood flow and required treatment for ischemia. Exemplary organs and/or tissues include, but are not limited to, brain, arteries, heart, intestines and eye (e.g., the optic nerve). Ischemia-induced injuries (i.e., disease and/or damage produced by various types of ischemia) include, but are not limited to, ischemic myelopathy, ischemic optic neuropathy, ischemic colitis, coronary heart disease, and/or cardiac heart disease (e.g., angina, heart attack, etc.), among others. Ischemia-induced injury thus may damage and/or kill cells and/or tissue, for example, producing necrotic (infarcted) tissue, inflammation, and/or tissue remodeling, among others, at affected sites within the body. Treatment according to aspects of the present application may reduce the incidence, extent, and/or severity of this injury.

In some embodiments, the amiloride, amiloride analog or a pharmaceutically acceptable salt or solvate thereof is given in a dose range of 0.1 mg-10 mg /kg body weight. In other embodiments, the pharmaceutical composition is administered within one hour of the onset of an ischemic event, within five hours of the onset of an ischemic event, or between one hour and five hours of the onset of an ischemic event.

FIG. 1 shows a flowchart 20 with exemplary steps 22, 24 that may be performed in a method of reducing nerve injury in an ischemic subject. The steps may be performed any suitable number of times and in any suitable combination. In the method, an ischemic subject (or subjects) may be selected for treatment, indicated at 22. An ASIC-selective inhibitor then may be administered to the ischemic subject (s), indicated at 24. Administration of the inhibitor to the ischemic subject may be in a therapeutically effect amount, to reduce ischemia-induced injury to the subject, for example, reducing the amount of brain damage resulting from a stroke.

A potential explanation for the efficacy of the ischemia treatment of FIG. 1 may be offered by the data of the present teachings (e.g., see Example 1). In particular, the damaging effects of ischemia may not be equal to acidosis, that is, acidification of tissue/cells via ischemia may not be sufficient to produce ischemia-induced injury. Instead, ischemia-induced injury may be caused, in many cases, by calcium flux into cells mediated by a member(s) of the ASIC family, particularly ASIC1a. Accordingly, selective inhibition of the channel activity of ASIC1a may reduce this harmful calcium flux, thereby reducing ischemia-induced injury.

Figure 2:
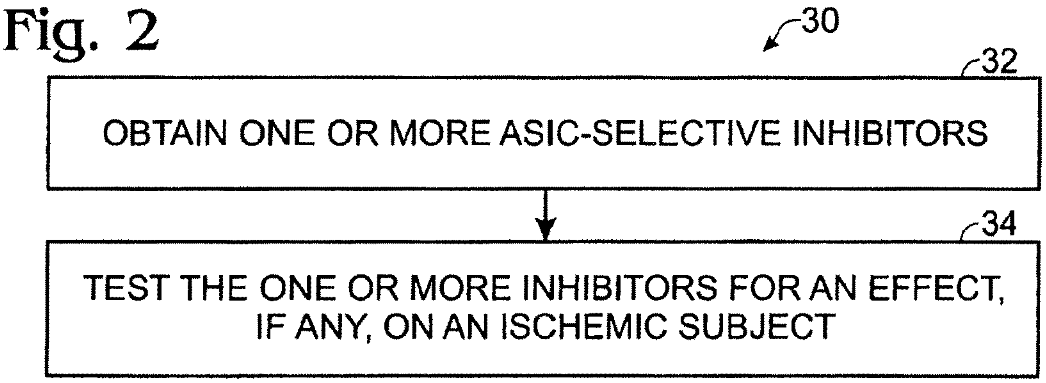
FIG. 2 is a view of a flowchart illustrating an exemplary method of identifying drugs for treating ischemia-related nerve injury.
Figure 3A:
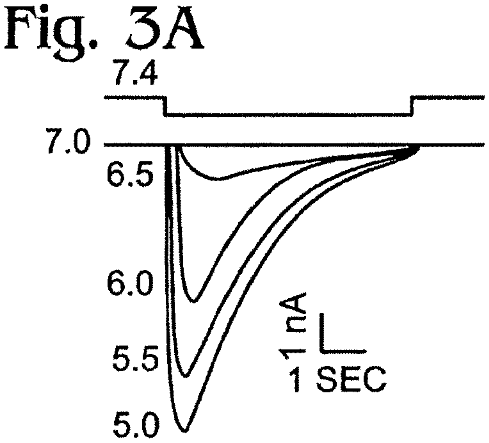
FIGS. 3A-D are a series of graphs presenting exemplary data related to the electrophysiology and pharmacology of acid sensing ion channel (ASIC) proteins in cultured mouse cortical neurons.
Figure 3B:
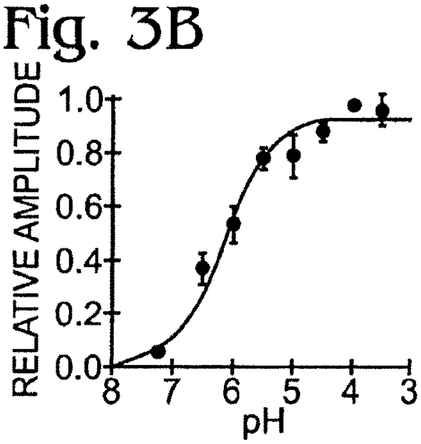
Figure 3C:
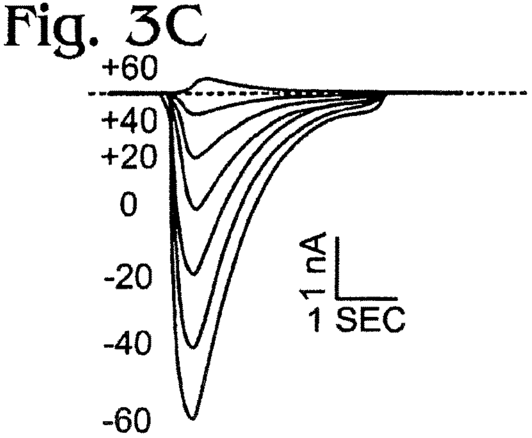
Figure 3D:
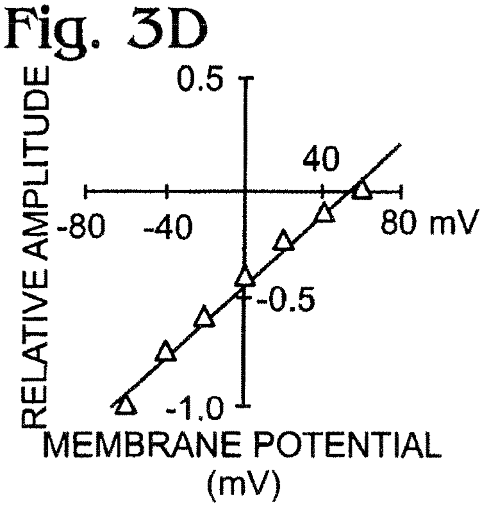
Figure 4A:
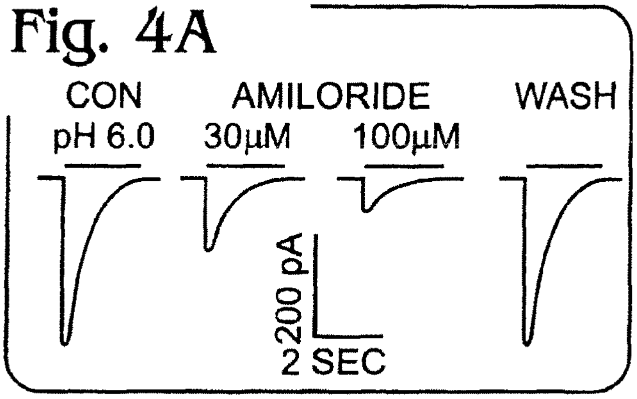
FIGS. 4A-D are an additional series of graphs presenting exemplary data related to the electrophysiology and pharmacology of ASIC proteins in cultured mouse cortical neurons.
Figure 4B:
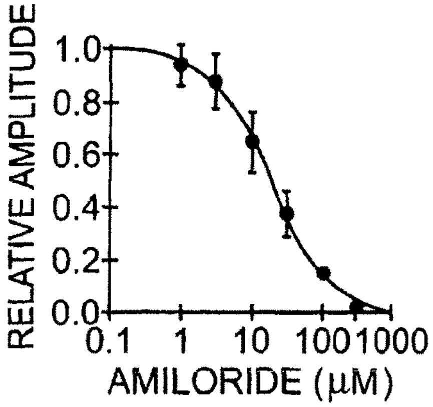
Figure 4C:
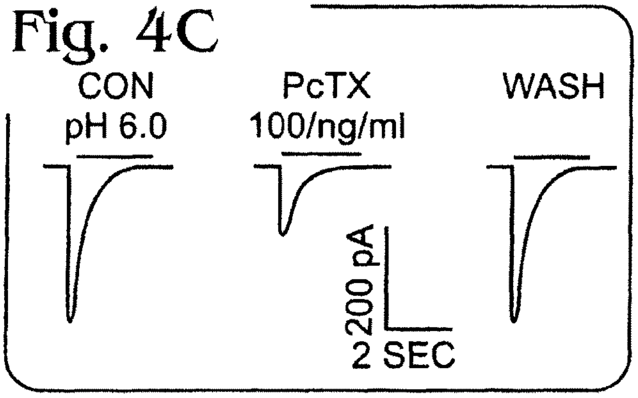
Figure 4D:
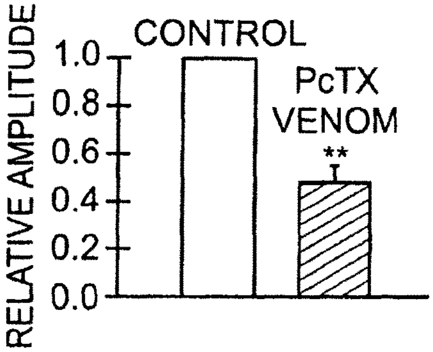
Figure 5A:
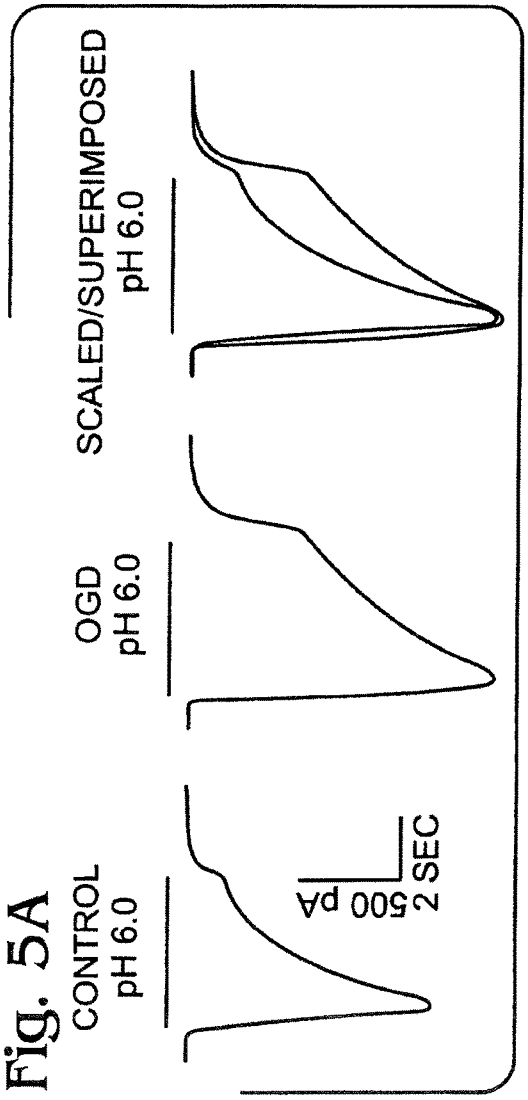
FIGS. 5A-D are a set of graphs and traces presenting exemplary data showing that modeled ischemia may enhance activity of ASIC proteins, in accordance with aspects of the present teachings.
Figure 5B:
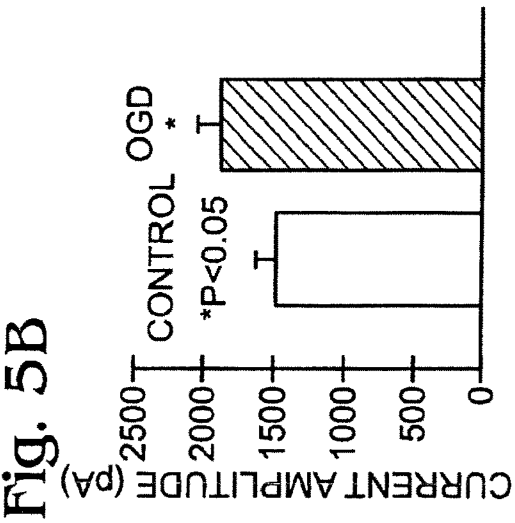
Figure 5C:
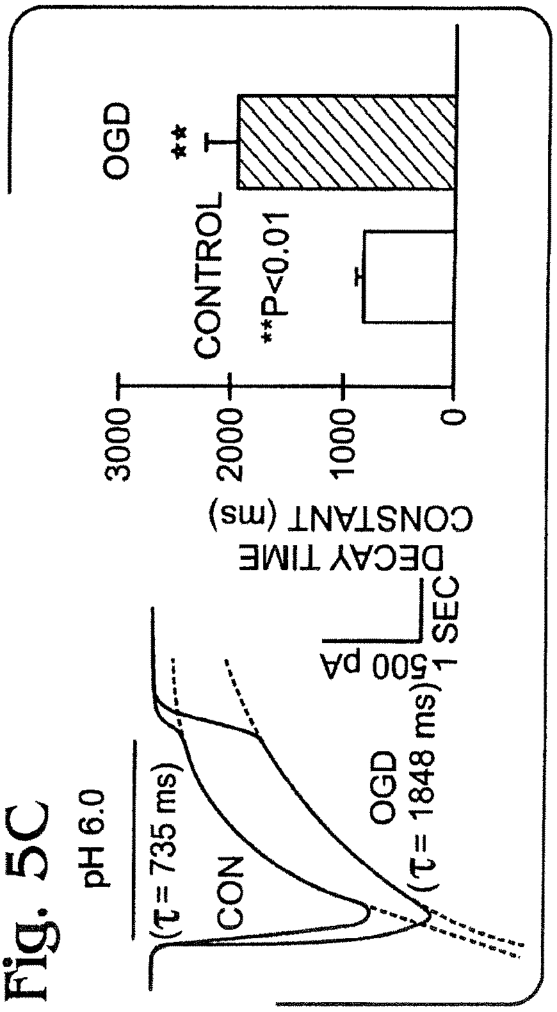
Figure 5D:
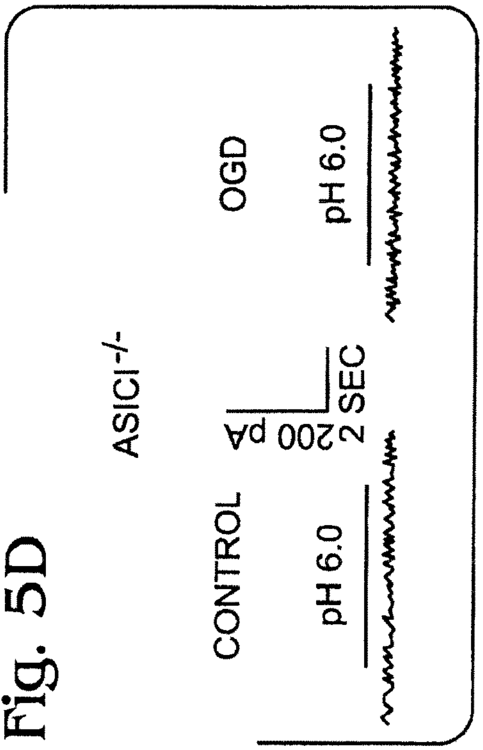

FIG. 2 shows a flowchart 30 with exemplary steps 32, 34 that may be performed in a method of identifying drugs for treatment of ischemia. The steps may be performed any suitable number of times and in any suitable combination. In the method, one or more ASIC-selective inhibitors may be obtained, indicated at 32. The inhibitors then may be tested on an ischemic subject for an effect on ischemia-induced injury, indicated at 34.

EXAMPLES

The following examples describe selected aspects and embodiments of the present teachings, particularly data describing in vitro and in vivo effects of ASIC inhibition. These examples are intended for the purposes of illustration and should not be construed to limit the scope of the present teachings.

Example 1: Neuroprotection in Ischemia by Blocking Calcium-Permeable Acid-Sensing Ion Channels This example describes experiments showing a role of ASIC1a in mediating ischemic injury and the ability ASIC1a inhibitors to reduce ischemic injury; see FIGS. 2-10. $Ca^{2+}$ toxicity may play a central role in ischemic brain injury. The mechanism by which toxic $Ca^{2+}$ loading of cells occurs in the ischemic brain has become less clear as multiple human trials of glutamate antagonists have failed to show effective neuroprotection in stroke. Acidosis is a common feature of ischemia and plays a critical role in brain injury. This example demonstrates that acidosis activates $Ca^{2+}$-permeable acid-sensing ion channels (ASICs), which may induce glutamate receptor-independent, $Ca^{2+}$-dependent, neuronal injury. Accordingly, cells lacking endogenous ASICs may be resistant to acid injury, while transfection of $Ca^{2+}$-permeable ASIC1a may establish sensitivity. In focal ischemia, intracerebroventricular injection of ASIC1a inhibitors or knockout of the ASIC1a gene may protect the brain from ischemic injury and may do so more potently than glutamate antagonism.

The normal brain requires complete oxidation of glucose to fulfill its energy requirements. During ischemia, oxygen depletion forces the brain to switch to anaerobic glycolysis. Accumulation of lactic acid as a byproduct of glycolysis and protons produced by ATP hydrolysis causes pH to fall in the ischemic brain and aggravates ischemic brain injury.

Acid-sensing ion channels (ASICs) are a class of ligand-gated channels expressed throughout neurons of mammalian central and peripheral nervous systems. To date, six ASIC subunits have been cloned. Four of these subunits form functional homomultimeric channels that are activated by acidic pH to conduct a sodium-selective, amiloride-sensitive, cation current. Two of the ASIC subunits, ASIC1a and ASIC2a subunits, have been shown to be abundant in the brain.

Experimental Procedures

Neuronal Culture

Following anesthesia with halothane, cerebral cortices were dissected from E16 Swiss mice or P1 $ASIC1^{+/+}$ and $ASIC1^{-/-}$ mice and incubated with 0.05% trypsin-EDTA for 10 min at 37° C. Tissues were then triturated with fire-polished glass pipettes and plated on poly-L-ornithine-coated 24-well plates or 25×25 mm glass coverslips at a density of $2.5\times10^5$ cells per well or $10^6$ cells per coverslip. Neurons were cultured with MEM supplemented with 10% horse serum (for E16 cultures) or Neurobasal medium supplemented with B27 (for P1 cultures) and used for electrophysiology and toxicity studies after 12 days. Glial growth was suppressed by addition of 5-fluoro-2-deoxyuridine and uridine, yielding cultured cells with 90% neurons as determined by NeuN and GFAP staining (data not shown).

Electrophysiology

ASIC currents were recorded with whole-cell patch-clamp and fast-perfusion techniques. The normal extracellular solution (ECF) contained (in mM) 140 NaCl, 5.4 KCl, 25 HEPES, 20 glucose, 1.3 $CaCl_2$, 1.0 $MgCl_2$, 0.0005 TTX (pH 7.4), 320-335 mOsm. For low pH solutions, various amounts of HCl were added. For solutions with pH<6.0, MES instead of HEPES was used for more reliable pH buffering. Patch electrodes contained (in mM) 140 CsF, 2.0 $MgCl_2$, 1.0 $CaC_2$, 10 HEPES, 11 EGTA, 4 MgATP (pH 7.3), 300 mOsm. The $Na^+$-free solution consisted of 10 mM $CaCl_2$, 25 mM HEPES with equiosmotic NMDG or sucrose substituting for NaCl (Chu et al., 2002). A multibarrel perfusion system (SF-77B, Warner Instrument Co.) was employed for rapid exchange of solutions.

Cell Injury Assay—LDH Measurement

Cells were washed three times with ECF and randomly divided into treatment groups. MK801 (10 μM), CNQX (20 μM), and nimodipine (5 μM) were added in all groups to eliminate potential secondary activation of glutamate receptors and voltage-gated $Ca^{2+}$ channels. Following acid incubation, neurons were washed and incubated in Neurobasal medium at 37° C. LDH release was measured in culture medium using the LDH assay kit (Roche Molecular Biochemicals). Medium (100 μL) was transferred from culture wells to 96-well plates and mixed with 100 μL reaction solution provided by the kit. Optical density was measured at 492 nm 30 min later, utilizing a microplate reader (Spectra Max Plus, Molecular Devices). Background absorbance at 620 was subtracted. The maximal releasable LDH was obtained in each well by 15 min incubation with 1% Triton X-100 at the end of each experiment.

$Ca^{2+}$ Imaging

Cortical neurons grown on 25×25 mm glass coverslips were washed three times with ECF, incubated with 5 μM fura-2-acetoxymethyl ester for 40 min at 22° C., washed three times, and then incubated in normal ECF for 30 min. Coverslips were transferred to a perfusion chamber on an inverted microscope (Nikon TE300). Cells were illuminated using a xenon lamp and observed with a 40× UV fluor oil-immersion objective lens, and video images were obtained using a cooled CCD camera (Sensys KAF 1401, Photometrics). Digitized images were acquired and analyzed in a PC controlled by Axon Imaging Workbench software (Axon Instruments). The shutter and filter wheel (Lambda 10-2) were controlled by the software to allow timed illumination of cells at 340 or 380 nm excitation wavelengths. Fura-2 fluorescence was detected at emission wavelength of 510 nm. Ratio images (340/380) were analyzed by averaging pixel ratio values in circumscribed regions of cells in the field of view. The values were exported to SigmaPlot for further analysis.

Fluorescein-Diacetate Staining and Propidium Iodide Uptake

Cells were incubated in ECF containing fluorescein-diacetate (FDA) (5 μM) and propidium iodide (PI) (2 μM) for 30 min followed by wash with dye-free ECF. Alive (FDA-positive) and dead (PI-positive) cells were viewed and counted on a microscope (Zeiss) equipped with epifluorescence at 580/630 nm excitation/emission for PI and 500/550 nm for FDA. Images were collected using an Optronics DEI-730 camera equipped with a BQ 8000 sVGA frame grabber and analyzed using computer software (Bioquant, Tenn.).

Transfection of COS-7 Cells

COS-7 cells were cultured in MEM with 10% HS and 1% PenStrep (GIBCO). At ~50% confluence, cells were cotransfected with cDNAs for ASICs and GFP in $pc^{DNA3}$ vector using FuGENE6 transfection reagents (Roche Molecular Biochemicals). DNA for ASICs (0.75 μg) and 0.25 μg of DNA for GFP were used for each 35 mm dish. GFP-positive cells were selected for patch-clamp recording 48 hr after transfection. For stable transfection of ASIC1a, 500 μg/mL G418 was added to culture medium I week following the transfection. The surviving G418-resistant cells were further plated and passed for >5 passages in the presence of G418. Cells were then checked with patch-clamp and immunofluorescent staining for the expression of ASIC1a.

Oxygen-Glucose Deprivation

Neurons were washed three times and incubated with glucose-free ECF at pH 7.4 or 6.0 in an anaerobic chamber (Model 1025, Forma Scientific) with an atmosphere of 85% $N_2$, 10% $H_2$, and 5% $CO_2$ at 35° C. Oxygen-glucose deprivation (OGD) was terminated after 1 hr by replacing the glucose-free ECF with Neurobasal medium and incubating the cultures in a normal cell culture incubator. With HEPES-buffered ECF used, 1 hr OGD slightly reduced pH from 7.38 to 7.28 (n=3) and from 6.0 to 5.96 (n=4).

Focal Ischemia

Transient focal ischemia was induced by suture occlusion of the middle cerebral artery (MCAO) in male rats (SD, 250-300 g) and mice (with congenic C57B16 background, ~25 g) anesthetized using 1.5% isoflurane, 70% $N_{20}O$, and 28.5% $O_2$ with intubation and ventilation. Rectal and temporalis muscle temperature was maintained at 37° C.±0.5° C. with a thermostatically controlled heating pad and lamp. Cerebral blood flow was monitored by transcranical LASER doppler. Animals with blood flow not reduced below 20% were excluded.

Animals were killed with chloral hydrate 24 hr after ischemia. Brains were rapidly removed, sectioned coronally at 1 mm (mice) or 2 mm (rats) intervals, and stained by immersion in vital dye (2%) 2,3,5-triphenyltetrazolium hydrochloride (TTC). Infarction area was calculated by subtracting the normal area stained with TTC in the ischemic hemisphere from the area of the nonischemic hemisphere. Infarct volume was calculated by summing infarction areas of all sections and multiplying by slice thickness. Rat intraventricular injection was performed by stereotaxic technique using a microsyringe pump with cannula inserted stereotactically at 0.8 mm posterior to bregma, 1.5 mm lateral to midline, and 3.8 mm ventral to the dura. All manipulations and analyses were performed by individuals blinded to treatment groups.

Results (a) Acidosis Activates ASICs in Mouse Cortical Neurons

FIGS. 3 and 4 shows exemplary data related to the electrophysiology and pharmacology of ASICs in cultured mouse cortical neurons. FIGS. 3A and 3B are graphs illustrating the pH dependence of ASIC currents activated by a pH drop from 7.4 to the pH values indicated. Dose-response curves were fit to the Hill equation with an average $pH_{0.5}$ of 6.18±0.06 (n=10). FIGS. 3C and 3D are graphs illustrating the current-voltage relationship of ASICs (n=5). The amplitudes of ASIC current at various voltages were normalized to that recorded at −60 mV. FIGS. 4A and 4B are graphs illustrating a dose-dependent blockade of ASIC currents by amiloride. $IC_{50}$=16.4±4.1 μM, N=8. FIGS. 4C and 4D are graphs illustrating a blockade of ASIC currents by PcTX venom. **p<0.01.

ASIC currents in cultured mouse cortical neurons were recorded (see FIG. 3). At a holding potential of −60 mV, a rapid reduction of extracellular pH ($pH_e$) to below 7.0 evoked large transient inward currents with a small steady-state component in the majority of neurons (FIG. 3A). The amplitude of inward current increased in a sigmoidal fashion as $pH_e$ decreased, yielding a $pH_{0.5}$ of 6.18±0.06 (n=10, FIG. 3B). A linear I-V relationship and a reversal close to the $Na^+$ equilibrium potential were obtained (n=6, FIGS. 3C and 3D). These data demonstrate that lowering $pH_e$ may activate typical ASICs in mouse cortical neurons.

The effect of amiloride, a nonspecific inhibitor of ASICs, on the acid-activated currents was tested (see FIG. 4). As shown in FIG. 4, amiloride dose-dependently blocked ASIC currents in cortical neurons with an IC50 of 16.4±4.1 μM (n=8, FIGS. 4A and 4B). The effect of PcTX venom on acid-activated current in cortical neurons is shown in FIG. 4C and 4D. At 100 ng/mL, PcTX venom reversibly blocked the peak amplitude of ASIC current by 47%±7% (n=15, FIGS. 4C and 4D), indicating significant contributions of homomeric ASIC1a to total acid-activated currents. Increasing PcTX concentration did not induce further reduction in the amplitude of ASIC current in the majority of cortical neurons (n=8, data not shown), indicating coexistence of PcTX-insensitive ASICs (e.g., heteromeric ASIC1a/2a) in these neurons.

(b) ASIC Response is Potentiated by Modeled Ischemia

FIG. 5 shows exemplary data indicating that modeled ischemia may enhance activity of ASICs. FIG. 5A is a series of exemplary traces showing an increase in amplitude and a decrease in desensitization of ASIC currents following 1 hr OGD. FIG. 5B is a graph of summary data illustrating an increase of ASIC current amplitude in OGD neurons. N=40 and 44, *p<0.05. FIG. 5C is a series of exemplary traces and summary data showing decreased ASIC current desensitization in OGD neurons. N=6, p<0.01. FIG. 5**D is a pair of exemplary traces showing lack of acid-activated current at pH 6.0 in $ASIC1^{-/-}$ neurons, in control condition, and following 1 hr OGD (n=12 and 13).

Since acidosis may be a central feature of brain ischemia, it was determined to test whether ASICs may be activated in ischemic conditions and whether ischemia may modify the properties of these channels; see FIG. 5. ASIC currents in neurons following 1 hr oxygen glucose deprivation (OGD) were recorded. Briefly, one set of cultures was washed three times with glucose-free extracellular fluid (ECF) and subjected to OGD, while control cultures were subjected to washes with glucose containing ECF and incubation in a conventional cell culture incubator. OGD was terminated after 1 hr by replacing glucose-free ECF with Neurobasal medium and incubating cultures in the conventional incubator. ASIC current was then recorded 1 hr following the OGD when there was no morphological alteration of neurons. OGD treatment induced a moderate increase of the amplitude of ASIC currents (1520±138 pA in control group, N=44; 1886±185 pA in neurons following 1 hr OGD, N=40, p<0.05, FIGS. 5A and 5B). More importantly, OGD induced a dramatic decrease in ASIC desensitization as demonstrated by an increase in time constant of the current decay (814.7±58.9 ms in control neurons, N=6; 1928.9±315.7 ms in neurons following OGD, N=6, p<0.01, FIGS. 5A and 5C). In cortical neurons cultured from $ASIC1^{-/-}$ mice, reduction of pH from 7.4 to 6.0 did not activate any inward current (n=52), similar to a previous study in hippocampal neurons (Wemmie et al., 2002). In these neurons, 1 hr OGD did not activate or potentiate acid-induced responses (FIG. 5D, n=12 and 13).

(c) Acidosis Induces Glutamate-Independent $Ca^{2+}$ Entry Via ASIC1a

Figure 6B:
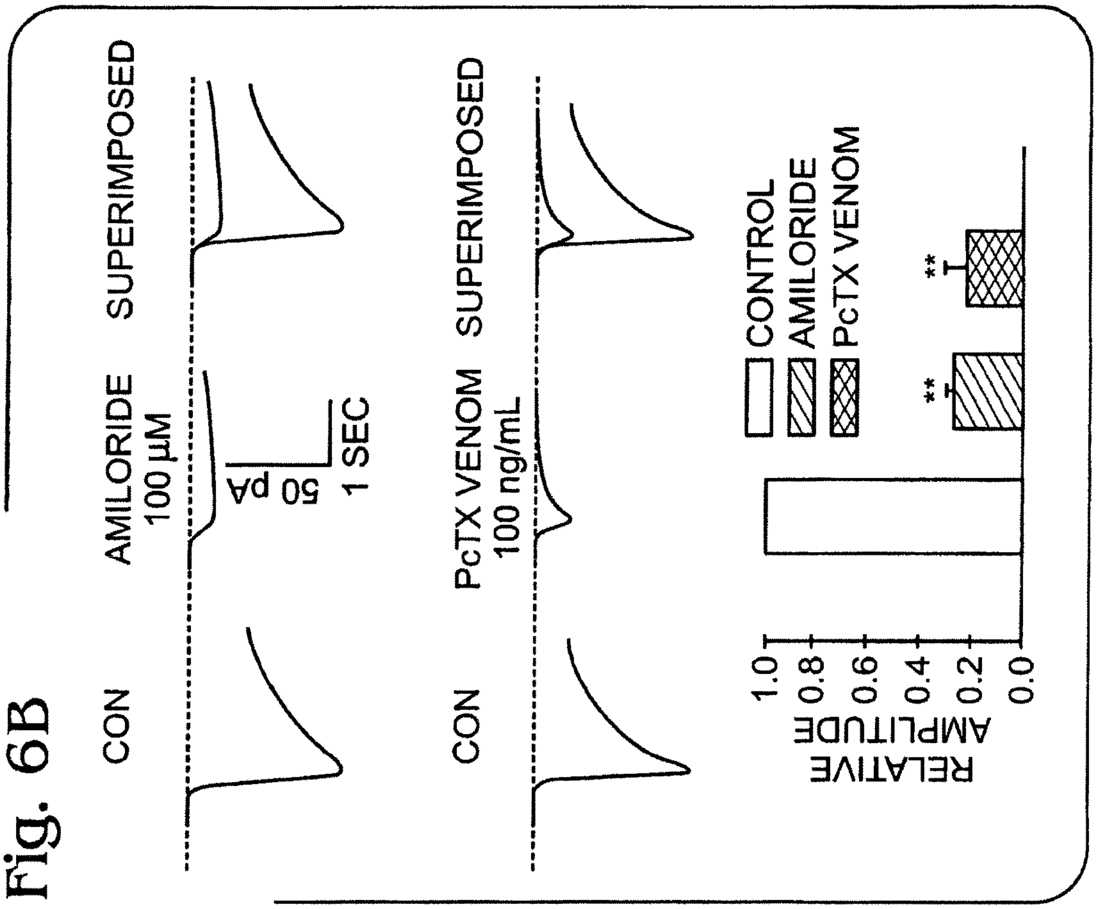
FIGS. 6A-B and 7A-D are a set of graphs and traces presenting exemplary data showing that ASIC proteins in cortical neurons may be $Ca^{2+}$ permeable, and that $Ca^{2+}$ permeability may be ASIC1a dependent.
Figure 6A:
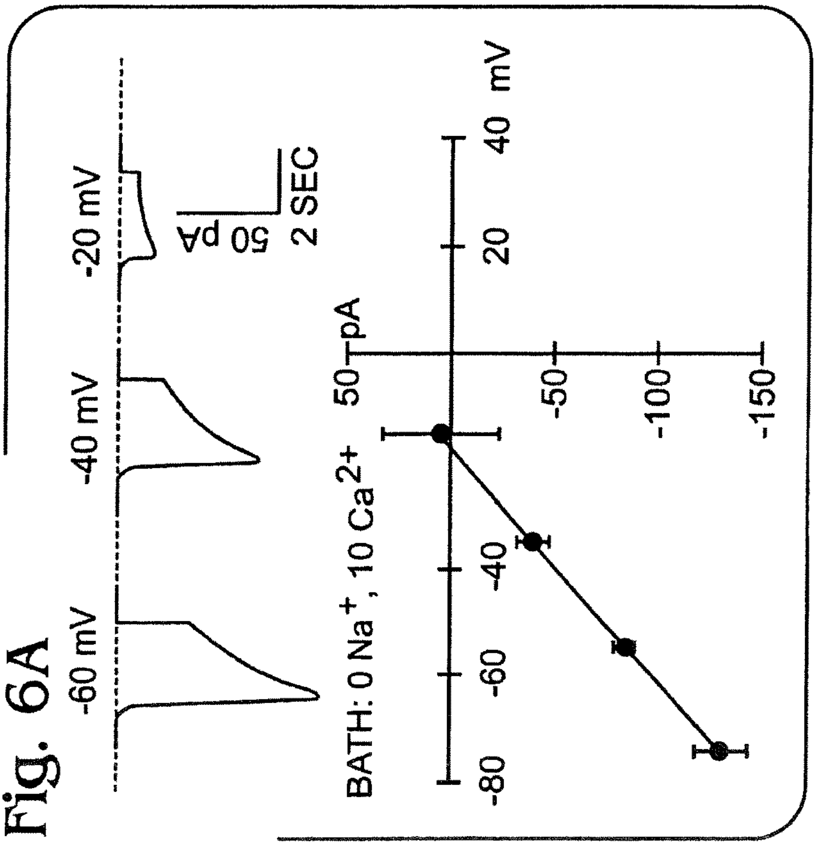
Figures 7A, 7B, 7C, 7D:
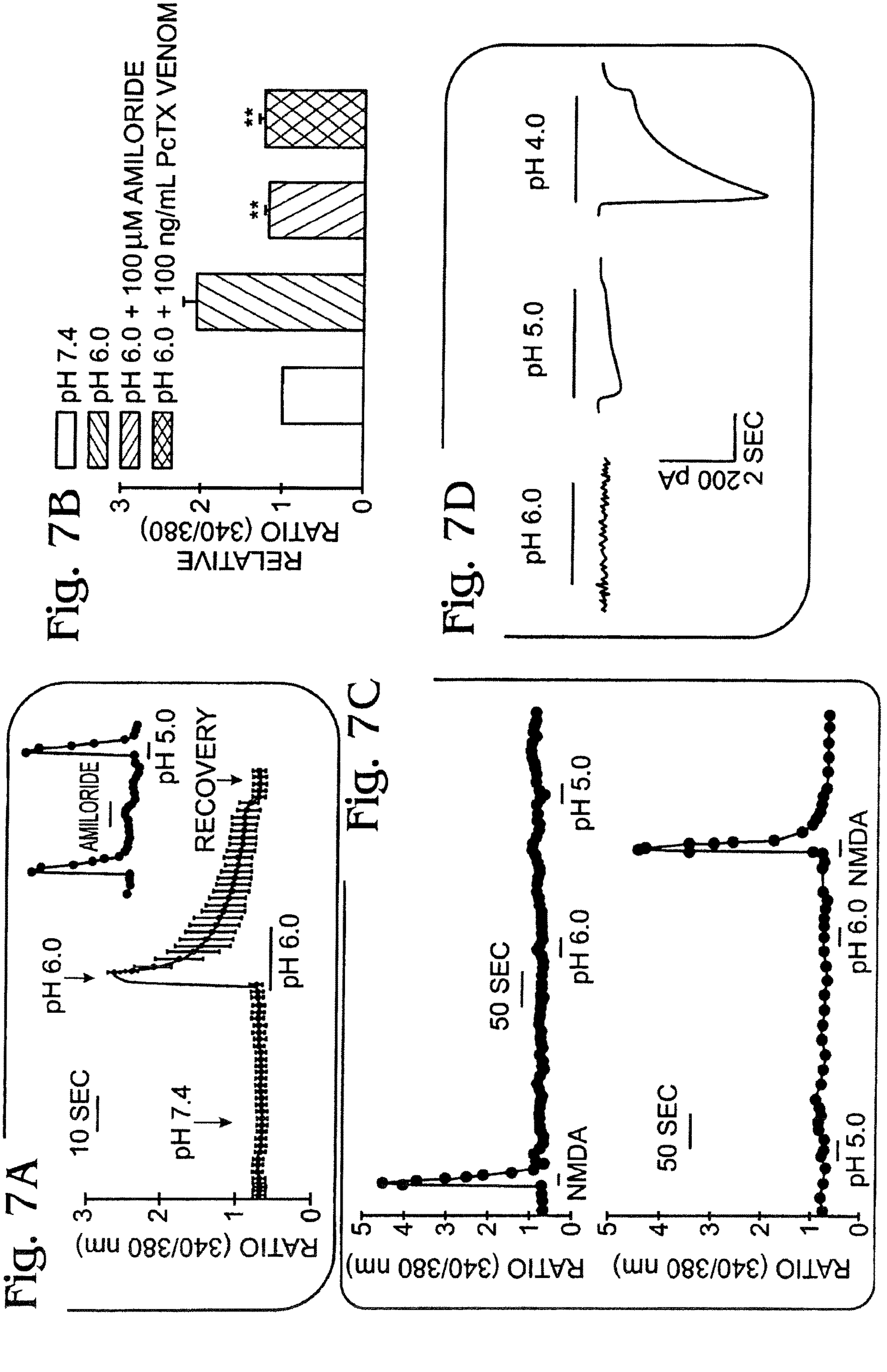

FIGS. 6 and 7 show exemplary data suggesting that ASICs in cortical neurons may be $Ca^{2+}$ permeable, and that $Ca^{2-}$ permeability may be ASIC1a dependent. FIG. 6A shows exemplary traces obtained with $Na^{+}$-free ECF containing 10 mM $Ca^{2+}$ as the only charge carrier. Inward currents were recorded at pH 6.0. The average reversal potential is ~−17 mV after correction of liquid junction potential (n=5). FIG. 6B shows representative traces and summary data illustrating blockade of $Ca^{2+}$-mediated current by amiloride and PcTX venom. The peak amplitude of $Ca^{2-}$-mediated current decreased to 26%±2% of control value by 100 μM amiloride (n=6, p<0.01) and to 22%±0.9% by 100 ng/mL PcTX venom (n=5, p<0.01). FIG. 7A shows exemplary 340/380 nm ratios as a function of pH, illustrating an increase of $[Ca^{2+}]_i$ by pH drop to 6.0. Neurons were bathed in normal ECF containing 1.3 mM $CaCl_2$ with inhibitors for voltage-gated $Ca^{2+}$ channels (5 μM nimodipine and 1 μM ω-conotoxin MVIIC) and glutamate receptors (10 μM MK801 and 20 μM CNQX). The inset of FIG. 7A shows exemplary inhibition of acid-induced increase of $[Ca^{2+}]_i$ by 100 μM amiloride. FIG. 7B shows exemplary summary data illustrating inhibition of acid-induced increase of $[Ca^{2+}]_i$ by amiloride and PcTX venom. N=6-8, p<0.01 compared with pH 6.0 group. FIG. 7C shows exemplary 340/380 nm ratios as a function of pH and NMDA presence/absence, demonstrating a lack of acid-induced increase of $[Ca^{2+}]_i$ in $ASIC1^{-/-}$ neurons; neurons had a normal response to NMDA (n=8). FIG. 7**D shows exemplary traces illustrating a lack of acid-activated current at pH 6.0 in $ASIC1^{-/-}$ neurons.

The $Ca^{2+}$ permeability of ASICs in cortical neurons was determined using a standard ion-substitution protocol (Jia et al., Neuron, 1996, 17:945-956) and the Fura-2 fluorescent $Ca^{2+}$-imaging technique (Chu et al., 2002, J. Neurophysiol. 87:2555-2561). With bath solutions containing 10 mM $Ca^{2+}$ ($Na^{+}$ and $K^{+}$-free) as the only charge carrier and at a holding potential of −60 mV, we recorded inward currents larger than 50 pA in 15 out of 18 neurons, indicating significant $Ca^{2+}$ permeability of ASICs in the majority of cortical neurons (FIG. 6A). Consistent with activation of homomeric ASIC1a channels, currents carried by 10 mM $Ca^{2+}$ were largely blocked by both the nonspecific ASIC inhibitor amiloride and the ASIC1a-specific inhibitor, PcTX venom (FIG. 6B). The peak amplitude of $Ca^{2+}$-mediated current was decreased to 26%±2% of control by 100 μM amiloride (n=6, p<0.01) and to 22%±0.9% by 100 ng/mL PcTX venom (n=5, p<0.01). $Ca^{2+}$ imaging, in the presence of inhibitors of other major $Ca^{2+}$ entry pathways (MK801 10 μM and CNQX 20 μM for glutamate receptors; nimodipine 5 μM and w-conotoxin MVIIC 1 μM for voltage-gated $Ca^{2+}$ channels), demonstrated that 18 out of 20 neurons responded to a pH drop with detectable increases in the concentration of intracellular $Ca^{2+}$ ($[Ca^{2+}]_i$) (FIG. 7A). In general, $[Ca^{2+}]_i$ remains elevated during prolonged perfusion of low pH solutions. In some cells, the $[Ca^{2+}]_i$ increase lasted even longer than the duration of acid perfusion (FIG. 7A). Long-lasting $Ca^{2+}$ responses suggest that ASIC response in intact neurons may be less desensitized than in whole-cell recordings or that $Ca^{2+}$ entry through ASICs may induce subsequent $Ca^{2+}$ release from intracellular stores. Preincubation of neurons with 1 μM thapsigargin partially inhibited the sustained component of $Ca^{2+}$ increase, suggesting that $Ca^{2+}$ release from intracellular stores may also contribute to acid-induced intracellular $Ca^{2+}$ accumulation (n=6, data not shown). Similar to the current carried by $Ca^{2+}$ ions (FIG. 6B), both peak and sustained increases in $[Ca^{2+}]_i$ were largely inhibited by amiloride and PcTX venom (FIGS. 7A and 7B, n=6-8), consistent with involvement of homomeric ASIC1a in acid-induced $[Ca^{2+}]_i$ increase. Knockout of the ASICI gene eliminated the acid-induced $[Ca^{2+}]_i$ increase in all neurons without affecting NMDA receptor-mediated $Ca^{2+}$ response (FIG. 7C, n=8). Patch-clamp recordings demonstrated lack of acid-activated currents at pH 6.0 in 52 out of 52 of the $ASIC1^{-/-}$ neurons, consistent with absence of ASIC1a subunits. Lowering pH to 5.0 or 4.0, however, activated detectable current in 24 out of 52 $ASIC1^{-/-}$ neurons, indicating the presence of ASIC2a subunits in these neurons (FIG. 7D). Further electrophysiological studies demonstrated that $ASIC1^{-/-}$ neurons have normal responses for various voltage-gated channels and NMDA, GABA receptor-gated channels (data not shown).

Figure 8A:
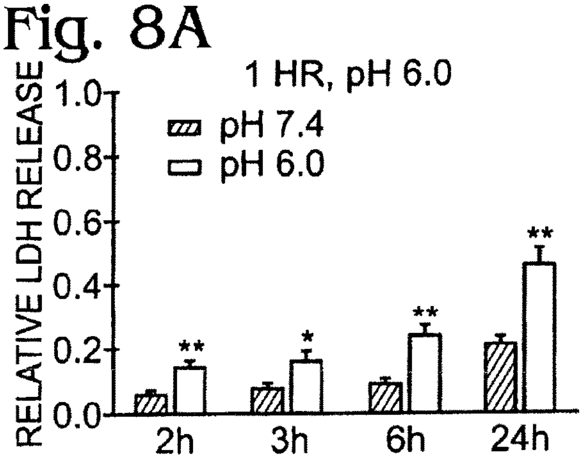
FIGS. 8A-C are a series of graphs presenting exemplary data showing that acid incubation may induce glutamate receptor-independent neuronal injury that is protected by ASIC blockade.
Figure 8B:
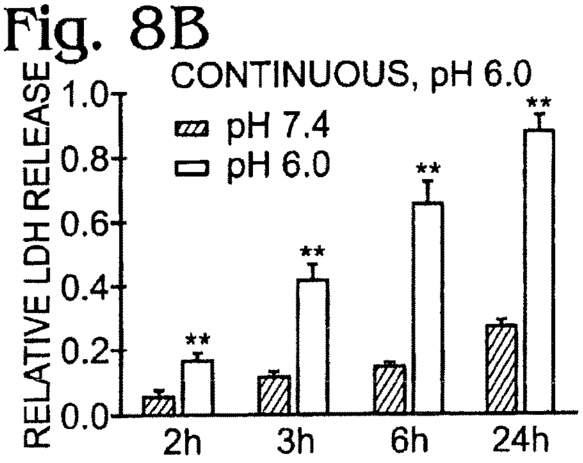

(d) ASIC Blockade Protects Acidosis-Induced, Glutamate-Independent Neuronal Injury FIG. 8 shows exemplary data suggesting that acid incubation may induce glutamate receptor-independent neuronal injury protected by ASIC blockade. FIGS. 8A and 8B show graphs presenting exemplary data for time-dependent LDH release induced by 1 hr (FIG. 8A) or 24 hr incubation (FIG. 8B) of cortical neurons in pH 7.4 (solid bars) or 6.0 ECF (open bars). N=20-25 wells, *p<0.05, and p<0.01, compared to pH 7.4 group at the same time points (acid-induced neuronal injury with fluorescein diacetate (FDA) also was analyzed by staining of cell bodies of alive neurons and propidium iodide (PI) staining of nuclei of dead neurons). FIG. 8**C shows a graph illustrating inhibition of acid-induced LDH release by 100 μM amiloride or 100 ng/mL PcTX venom (n=20-27, *p<0.05, and p<0.01). MK801, CNQX, and nimodipine were present in ECF for all experiments (FIGS. 8**A-C).

Acid-induced injury was studied on neurons grown on 24-well plates incubated in either pH 7.4 or 6.0 ECF containing MK801, CNQX, and nimodipine; see FIG. 8. Cell injury was assayed by the measurement of lactate dehydrogenase (LDH) release (Koh and Choi, J. Neurosci., 1987, 20:83-90) at various time points (FIGS. 8A and 8B) and by fluorescent staining of alive/dead cells. Compared to neurons treated at pH 7.4, 1 hr acid incubation (pH 6.0) induced a time-dependent increase in LDH release (FIG. 8A). After 24 hr, 45.7%±5.4% of maximal LDH release was induced (n=25 wells). Continuous treatment at pH 6.0 induced greater cell injury (FIG. 8B, n=20). Consistent with the LDH assay, alive/dead staining with fluorescein diacetate and propidium iodide showed similar increases in cell death by 1 hr acid treatment (data not shown). One hour incubation with pH 6.5 ECF also induced significant but less LDH release than with pH 6.0 ECF (n=8 wells, data not shown).

Figure 8C:
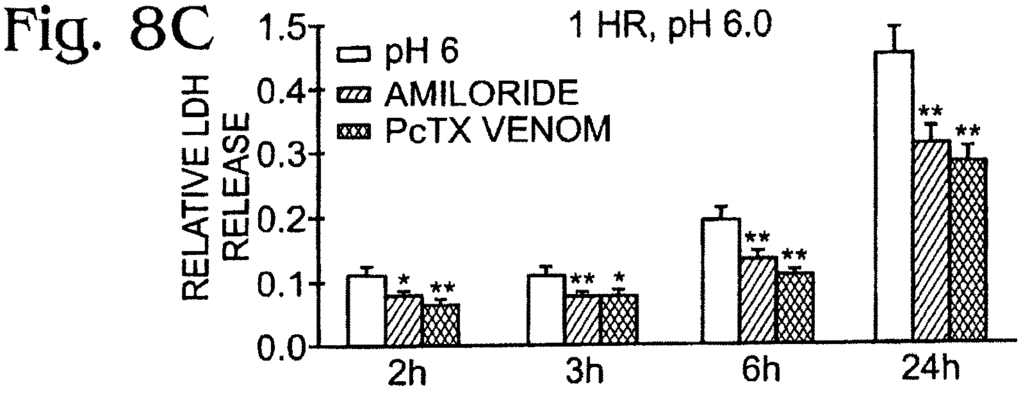

The effects of amiloride and PcTX venom on acid-induced LDH release were tested to determine whether activation of ASICs is involved in acid-induced glutamate receptor-independent neuronal injury. Addition of either 100 μM amiloride or 100 ng/mL PcTX venom 10 min before and during the 1 hr acid incubation significantly reduced LDH release (FIG. 8C). At 24 hr, LDH release was decreased from 45.3%±3.8% to 31.1%±2.5% by amiloride and to 27.9%±2.6% by PcTX venom (n=20-27, p<0.01). Addition of amiloride or PcTX venom in pH 7.4 ECF for 1 hr did not affect baseline LDH release, although prolonged incubation (e.g., 5 hr) with amiloride alone increased LDH release (n=8, data not shown).

(e) Activation of Homomeric ASIC1a is Responsible for Acidosis-Induced Injury

FIG. 9 is a series of graphs presenting exemplary data indicating that ASIC1a may be involved in acid-induced injury in vitro. FIG. 9A shows exemplary data illustrating inhibition of acid-induced LDH release by reducing $[Ca^{2+}]_e$ (n=11-12, p<0.01 compared with pH 6.0, 1.3 $Ca^{2+}$). FIG. 9**B shows exemplary data illustrating acid incubation induced increase of LDH release in ASIC1a-transfected but not nontransfected COS-7 cells (n=8-20). Amiloride (100 μM) inhibited acid-induced LDH release in ASIC1a-transfected cells. *p<0.05 for 7.4 versus 6.0 and 6.0 versus 6.0+amiloride. FIG. 9C shows exemplary data illustrating a lack of acid-induced injury and protection by amiloride and PcTX venom in $ASIC1^{-/-}$ neurons (n=8 in each group, p>0.05). FIG. 9D shows exemplary data illustrating acid-induced increase of LDH release in cultured cortical neurons under OGD (n=5). LDH release induced by combined 1 hr OGD/acidosis was not inhibited by trolox and L-NAME (n=8-11). OGD did not potentiate acid-induced LDH release in $ASIC1^{-/-}$ neurons. **p<0.01 for pH 7.4 versus pH 6.0 and *p<0.05 for pH 6.0 versus 6.0+PcTX venom. MK801, CNQX, and nimodipine were present in ECF for all experiments (FIG. 9A-D).

Neurons were treated with pH 6.0 ECF in the presence of normal or reduced $[Ca^{2+}]_e$ to determine whether $Ca^{2+}$ entry plays a role in acid-induced injury (see FIG. 9). Reducing $Ca^{2+}$ from 1.3 to 0.2 mM inhibited acid-induced LDH release (from 40.0%±4.1% to 21.9%±2.5%), as did ASIC1a blockade with PcTX venom (n=11-12, p<0.01; FIG. 9A). $Ca^{2+}$-free solution was not tested, as a complete removal of $[Ca^{2+}]_e$ may activate large inward currents through a $Ca^{2+}$-sensing cation channel, which may otherwise complicate data interpretation. Inhibition of acid injury by both amiloride and PcTX, nonspecific and specific ASIC1a inhibitors, and by reducing $[Ca^{2-}]_e$ suggests that activation of $Ca^{2+}$-permeable ASIC1a may be involved in acid-induced neuronal injury.

Figure 9A:
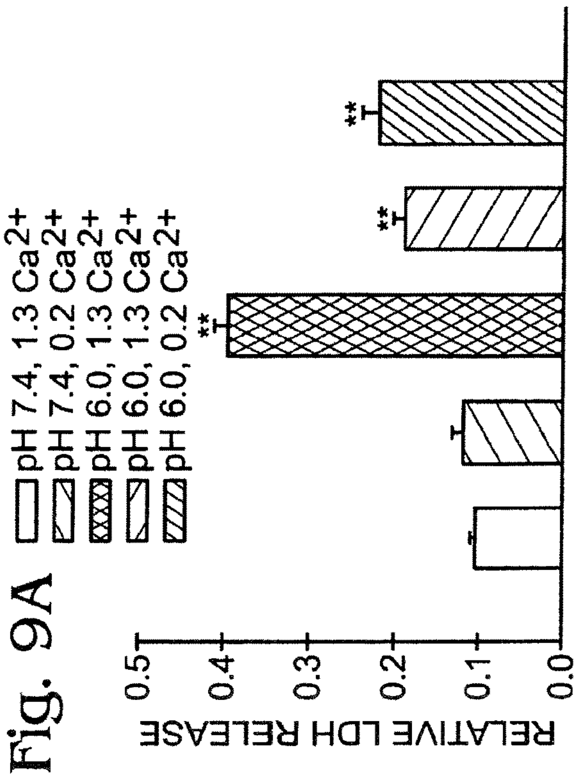
FIGS. 9A-D are a series of graphs presenting exemplary data showing that ASIC1a may be involved in acid-induced injury in vitro.
Figure 9B:
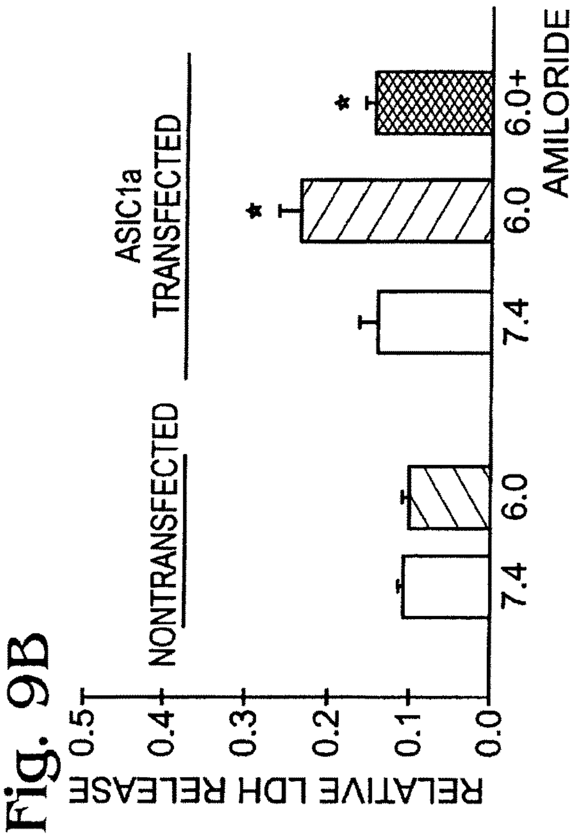

Acid injury of nontransfected and ASIC1a transfected COS-7 cells was studied to provide additional evidence that activation of ASIC1a is involved in acid injury. COS-7 is a cell line commonly used for expression of ASICs due to its lack of endogenous channels. Following confluence (36-48 hr after plating), cells were treated with either pH 7.4 or 6.0 ECF for 1 hr. LDH release was measured 24 hr after acid incubation. Treatment of nontransfected COS-7 cells with pH 6.0 ECF did not induce increased LDH release when compared with pH 7.4-treated cells (10.3%±0.8% for pH 7.4, and 9.4%±0.7% for pH 6.0, N=19 and 20 wells; p>0.05, FIG. 9B). However, in COS-7 cells stably transfected with ASIC1a, 1 hr incubation at pH 6.0 significantly increased LDH release from 15.5%±2.4% to 24.0%±2.9% (n=8 wells, p<0.05). Addition of amiloride (100 μM) inhibited acid-induced LDH release in these cells (FIG. 9B).

Acid injury of CHO cells transiently transfected with cDNAs encoding GFP alone or GFP plus ASIC1a was also studied. After the transfection (24-36 hr), cells were incubated with acidic solution (pH 6.0) for 1 hr, and cell injury was assayed 24 hr following the acid incubation. One hour acid incubation largely reduced surviving GFP-positive cells in GFP/ASIC1a group but not in the group transfected with GFP alone (data not shown).

Figure 9C:
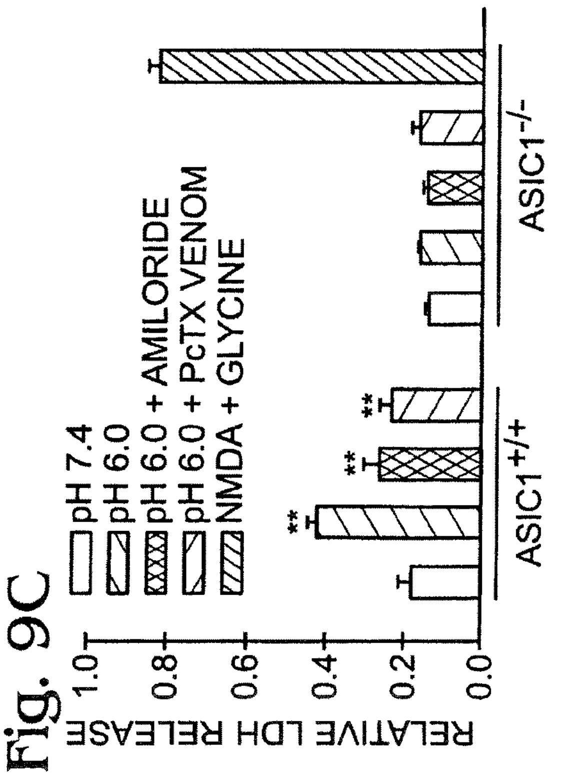

Cell toxicity experiments on cortical neurons cultured from $ASIC^{+/+}$ and $ASIC1^{-/-}$ mice were performed to further demonstrate an involvement of ASIC1a in acidosis-induced neuronal injury. Again, 1 hr acid incubation of $ASIC^{+/+}$ neurons at 6.0 induced substantial LDH release that was reduced by amiloride and PcTX venom (n=8-12). One hour acid treatment of $ASIC1^{-/-}$ neurons, however, did not induce significant increase in LDH release at 24 hr (13.8%±0.9% for pH 7.4 and 14.2%±1.3% for pH 6.0, N=8, p>0.05), indicating resistance of these neurons to acid injury (FIG. 9C). In addition, knockout of the ASIC1 gene also eliminated the effect of amiloride and PcTX venom on acid-induced LDH release (FIG. 9C, n=8 each), further suggesting that the inhibition of acid-induced injury of cortical neurons by amiloride and PcTX venom (FIG. 8C) was due to blockade of ASIC1 subunits. In contrast to acid incubation, 1 hr treatment of $ASIC1^{-/-}$ neurons with 1 mM NMDA+10 μM glycine (in $Mg^{2+}$-free [pH 7.4] ECF) induced 84.8%±1.4% of maximal LDH release at 24 hr (n=4, FIG. 9C), indicating normal response to other cell injury processes.

(n Modeled ischemia enhances acidosis-induced glutamate-independent neuronal injury via ASICs As the magnitude of ASIC currents may be potentiated by cellular and neurochemical components of brain ischemia-cell swelling, arachidonic acid, and lactate and, more importantly, the desensitization of ASIC currents may be reduced dramatically by modeled ischemia (see FIGS. 5A and 5C), activation of ASICs in ischemic conditions is expected to produce greater neuronal injury. To test this hypothesis, neurons were subjected to 1 hr acid treatment under oxygen and glucose deprivation (OGD). MK801, CNQX, and nimodipine were added to all solutions to inhibit voltage-gated $Ca^{2+}$ channels and glutamate receptor-mediated cell injury associated with OGD. One hour incubation with pH 7.4 ECF under OGD conditions induced only 27.1%±3.5% of maximal LDH release at 24 hr (n=5, FIG. 9D). This finding is in agreement with a previous report that 1 hr OGD does not induce substantial cell injury with the blockade of glutamate receptors and voltage-gated $Ca^{2+}$ channels (Aarts et al., 2003). However, 1 hr OGD, combined with acidosis (pH 6.0), induced 73.9%±4.3% of maximal LDH release (n=5, FIG. 9D, p<0.01), significantly larger than acid-induced LDH release in the absence of OGD (see FIG. 8A, p<0.05). Addition of the ASIC1a inhibitor PcTX venom (100 ng/mL) significantly reduced acid/OGD-induced LDH release to 44.3%±5.3% (n=5, p<0.05, FIG. 9D).

The same experiment was performed with cultured neurons from the $ASIC1^{-/-}$ mice. Unlike in ASICI containing neurons, however, 1 hr treatment with combined OGD and acid only slightly increased LDH release in $ASIC1^{-/-}$ neurons (from 26.1%±2.7% to 30.4%±3.5%, N=10-12, FIG. 9D). This finding suggests that potentiation of acid-induced injury by OGD may be due largely to OGD potentiation of ASIC1-mediated toxicity.

Figure 9D:
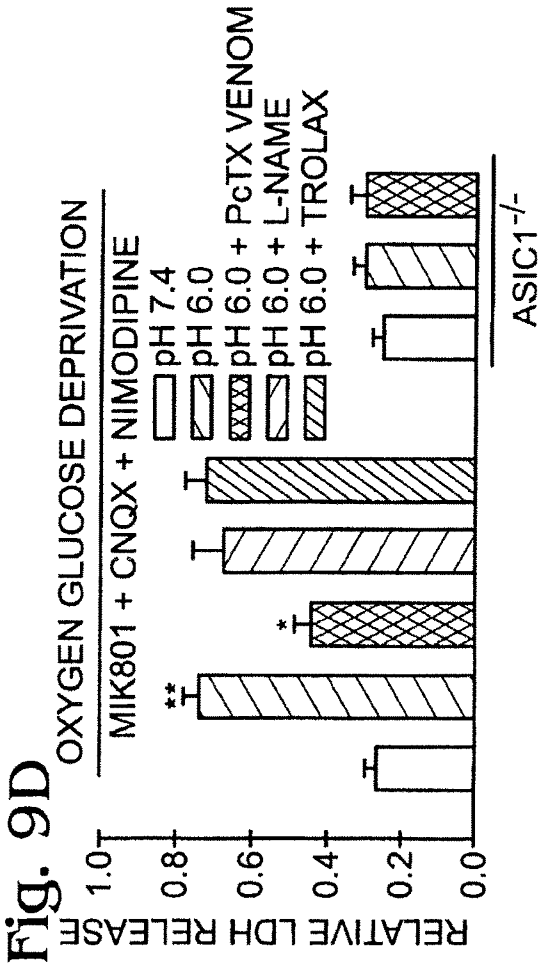

It has been demonstrated that activation of a $Ca^{2+}$-permeable nonselective cation conductance activated by reactive oxygen/nitrogen species resulting in glutamate receptor-independent neuronal injury (Aarts et al, Cell, 2003, 115: 863-877) . The prolonged OGD-induced cell injury may be reduced dramatically by agents either scavenging free radicals directly (e.g., trolox) or reducing the production of free radicals (e.g., L-NAME). To determine whether combined short duration OGD and acidosis induced neuronal injury may involve a similar mechanism, the effect of trolox and L-NAME on OGD/acid-induced LDH release was tested. As shown in FIG. 9D, neither trolox (500 μM) nor L-NAME (300 μM) had significant effect on combined 1 hr OGD/acidosis-induced neuronal injury (n=8-11). Additional experiments also demonstrated that the ASIC inhibitors amiloride and PcTX venom had no effect on the conductance of TRPM7 channels (Aarts et al. supra). Together, these findings strongly suggest that activation of ASICs but not TRPM7 channels may be largely responsible for combined 1 hr OGD/acidosis-induced neuronal injury in our studies.

(g) Activation of ASIC1a in Ischemic Brain Injury In Vivo

FIG. 10 shows data illustrating neuroprotection by ASICI blockade and ASICI gene knockout in brain ischemia in vivo. FIG. 10A shows a graph of exemplary data obtained from TTC-stained brain sections illustrating the stained volume ("infarct volume") in brains from aCSF (n=7), amiloride (n=11), or PcTX venom (n=5) injected rats. *p<0.05 and **p<0.01 compared with aCSF injected group. FIG. 10B shows a graph of exemplary data illustrating reduction in infarct volume in brains from $ASIC1^{-/-}$ mice (n=6 for each group). *p<0.05 and p<0.01 compared with +/+ group. FIG. 10C shows a graph of exemplary data illustrating reduction in infarct volume in brains from mice i.p. injected with 10 mg/kg memantine (Mem) or i.p. injection of memantine accompanied by i.c.v. injection of PcTX venom (500 ng/mL). p<0.01 compared with aCSF injection and between memantine and memantine plus PcTX venom (n=5 in each group). FIG. 10D shows a graph of exemplary data illustrating reduction in infarct volume in brains from either $ASIC1^{+/+}$ (wt) or $ASIC1^{-/-}$ mice i.p. injected with memantine (n=5 in each group). *p<0.05, and **p<0.01.

Figure 10A:
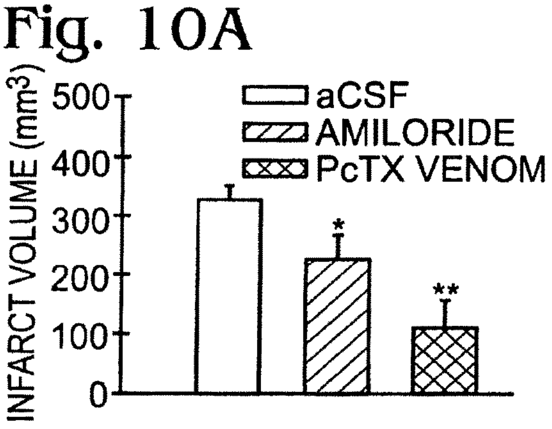
FIGS. 10A-D are a series of graphs with data showing neuroprotection in brain ischemia in vivo by ASIC1a blockade and by ASIC1 gene knockout.

The protective effect of amiloride and PcTX venom in a rat model of transient focal ischemia (Longa et al., Stroke, 1989, 20:84-91) was tested to determine whether activation of ASIC1a is involved in ischemic brain injury in vivo. Ischemia (100 min) was induced by transient middle cerebral artery occlusion (MCAO). A total of 6 μl artificial CSF (aCSF) alone, aCSF-containing amiloride (1 mM), or PcTX venom (500 ng/mL) was injected intracerebroventricularly 30 min before and after the ischemia. The volume for cerebral ventricular and spinal cord fluid for 4-week-old rats is estimated to be ~60 μl. Assuming that the infused amiloride and PcTX were uniformly distributed in the CSF, a concentration of ~100 μM for amiloride and ~50 ng/mL for PcTX were expected, which is a concentration found effective in cell culture experiments. Infarct volume was determined by TTC staining (Bederson et al., Stroke, 1986, 17:1304-1308) at 24 hr following ischemia. Ischemia (100 min) produced an infarct volume of 329.5±25.6 $mm^3$ in aCSF-injected rats (n=7) but only 229.7±41.1 $mm^3$ in amiloride-injected (n=11, p<0.05) and 130.4±55.0 $mm^3$ (~60% reduction) in PcTX venom-injected rats (n=5, p<0.01) (FIG. 10A).

Figure 10B:
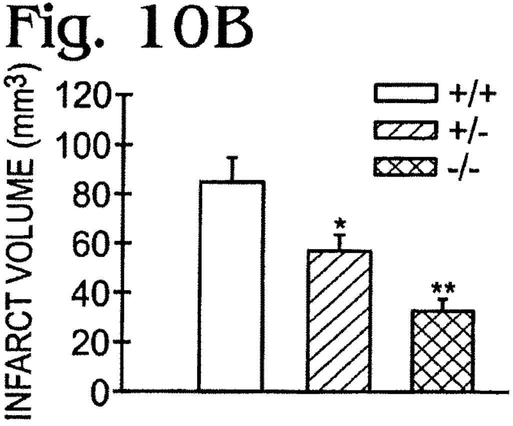
Figure 10C:
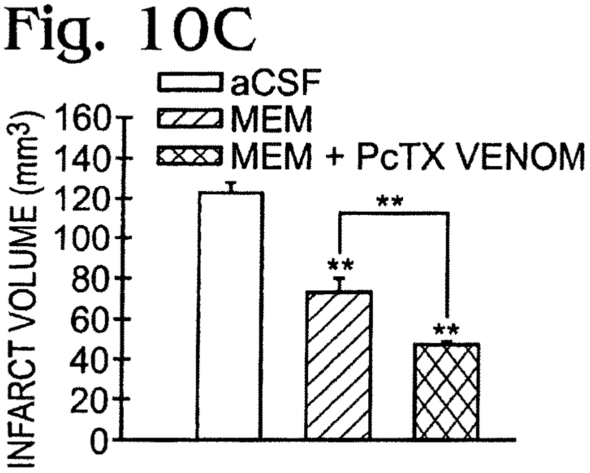

$ASIC1^{-/-}$ mice were used to further demonstrate the involvement of ASIC1a in ischemic brain injury in vivo. Male $ASIC1^{+/+}$, $ASIC1^{+/-}$, and $ASIC1^{-/-}$ mice (~25 g, with congenic C57B16 background) were subjected to 60 min MCAO as previously described (Stenzel-Poore et al., Lancet, 2003, 362:1028-1037). Consistent with the protection by pharmacological blockade of ASIC1a (above), −/− mice displayed significantly smaller (~61% reduction) infarct volumes (32.9±4.7 $mm^3$, N=6) as compared to +/+ mice (84.6±10.6 $mm^3$, N=6, p<0.01).+/− mice also showed reduced infarct volume (56.9 +-.6.7 $mm^3$, N=6, p<0.05) (FIG. 10B).

Figure 10D:
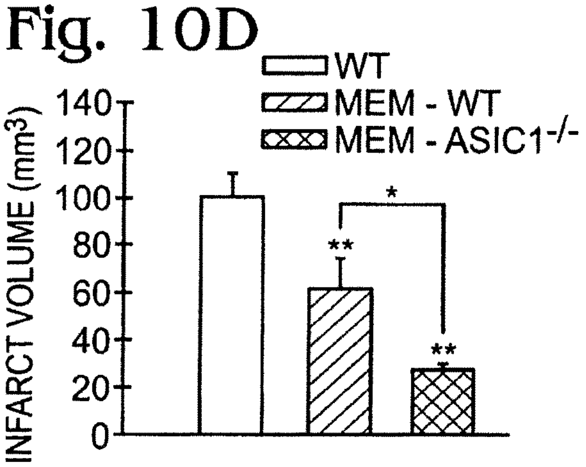

To determine whether blockade of ASIC1a channels or knockout of the ASIC1 gene would provide additional protection in vivo in the setting of glutamate receptor blockade, memantine (10 mg/kg) was injected intraperitoneally (i.p.) into C57B16 mice immediately following 60 min MCAO and accompanied by intracerebroventricular injection (i. c. v.) of a total volume of 0.4 μl aCSF alone or aCSF containing PcTX venom (500 ng/mL) 15 min before and following ischemia. In control mice with i.p. injection of saline and i.c.v. injection of aCSF, 60 min MCAO induced an infarct volume of 123.6±5.3 $mm^3$ (n=5, FIG. 10C). In mice with intraperitoneal injection of memantine and intracerebroventricular injection of aCSF, the same duration of ischemia induced an infarct volume of 73.8+−0.6.9 $mm^3$ (n=5, p<0.01). However, in mice injected with memantine and PcTX venom, an infarct volume of only 47.0±1.1 $mm^3$ was induced (n=5, p<0.01 compared with both control and memantine groups, FIG. 10C). These data suggest that blockade of homomeric ASIC1a may provide additional protection in in vivo ischemia in the setting of NMDA receptor blockade. Additional protection was also observed in $ASIC1^{-/-}$ mice treated with pharmacologic NMDA blockade (FIG. 10D). In $ASIC^{+/+}$ mice i.p. injected with saline or 10 mg/kg memantine, 60 min MCAO induced an infarct volume of 101.4±9.4 $mm^3$ or 61.6±12.7 $mm^3$, respectively (n=5 in each group, FIG. 10D). However, in $ASIC1^{-/-}$ mice injected with memantine, the same ischemia duration induced an infarct volume of 27.7±1.6 $mm^3$ (n=5), significantly smaller than the infarct volume in $ASIC1^{+/+}$ mice injected with memantine (p<0.05).

Taken together, these data demonstrate that activation of $Ca^{2+}$-permeable ASIC1a is a novel, glutamate-independent biological mechanism underlying ischemic brain injury.

Example 2: Time Window of PcTX Neuroprotection

Figure 11:
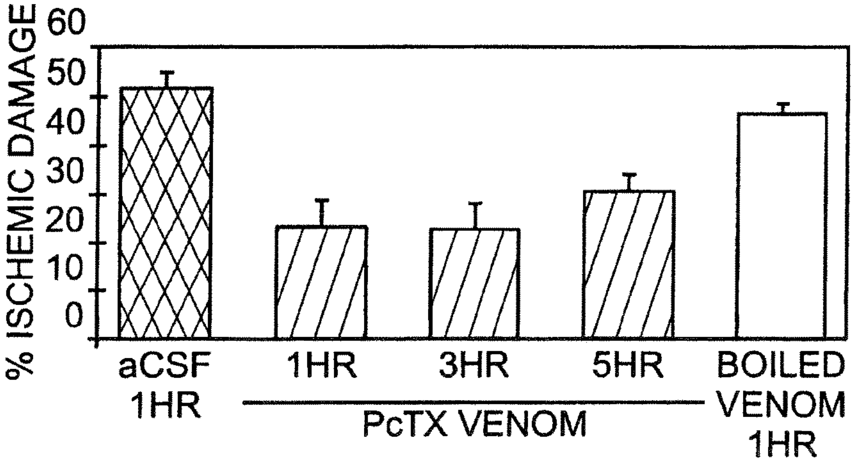
FIG. 11 is a graph plotting exemplary data for the percentage of ischemic damage produced by stroke in an animal model system as a function of the time and type of treatment.

This example describes exemplary experiments that measure the neuroprotective effect of PcTX venom at different times after onset of stroke in rodents; see FIG. 11. Briefly, brain ischemia (stroke) was induced in rodents by mid-cerebral artery occlusion (MCAO). At the indicated times after induction, artificial cerebrospinal fluid (aCSF), PcTX venom (0.5 μL, 500 ng/mL total protein), or inactivated (boiled) venom was infused into the lateral ventricles of each rodent. As shown in FIG. 11, administration of PcTX venom provided a 60% reduction in stroke volume both at one hour and at three hours after stroke onset. Furthermore, substantial stroke volume reduction still may be maintained if treatment is withheld for five hours after the onset of the MCAO. Accordingly, neuroprotection due to ASIC inhibition may have an extended therapeutic time window after stroke onset, allowing stroke subjects to benefit from treatment performed hours after the stroke began. This effect of ASIC blockade on stroke neuroprotection is far more robust than that of calcium channel blockade of the NMDA receptor (a major target for experimental stroke therapeutics) using a glutamate antagonist. No glutamate antagonist, thus far, has such a favorable profile as shown here for ASIC1a-selective inhibition.

Example 3: Exemplary Cystine Knot Peptides

This example describes exemplary cystine knot peptides, including full-length PcTx1 and deletion derivatives of PcTx, which may be screened in cultured cells, tested in ischemic animals (e.g., rodents such as mice or rats), and/or administered to ischemic human subjects.

Figure 12:
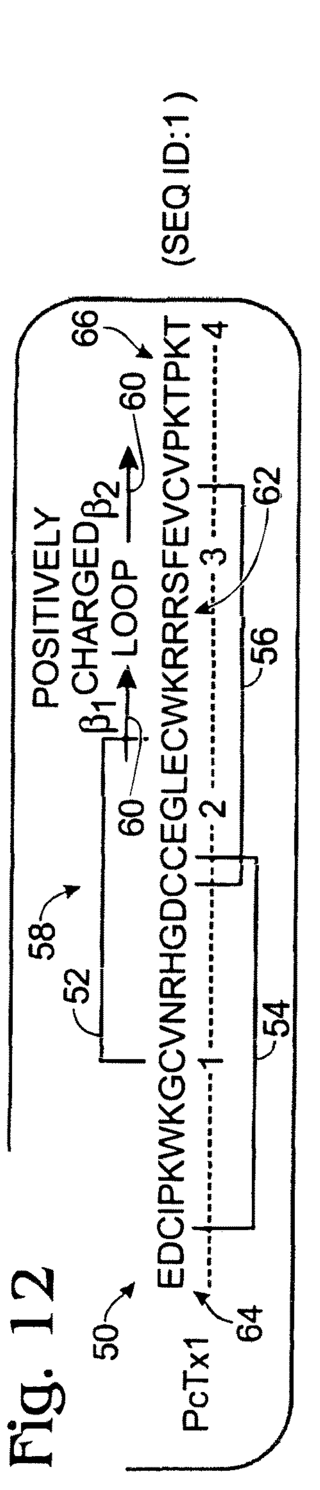
FIG. 12 is a view of the primary amino acid sequence of an exemplary cystine knot peptide, PcTx1 (SEQ. ID. NO. 1), with various exemplary peptide features shown.

FIG. 12 shows the primary amino acid sequence (SEQ ID NO:1), in one-letter code, of an exemplary cystine knot peptide, PcTx1, indicated at 50, with various exemplary peptide features shown relative to amino acid positions 1-40. Peptide 50 may include six cysteine residues that form cystine bonds 52, 54, 56 to create a cystine knot motif 58. The peptide also may include one or more beta sheet regions 60 and a positively charged region 62. An N-terminal region 64 and a C-terminal region 66 may flank the cystine knot motif.

Figure 13:
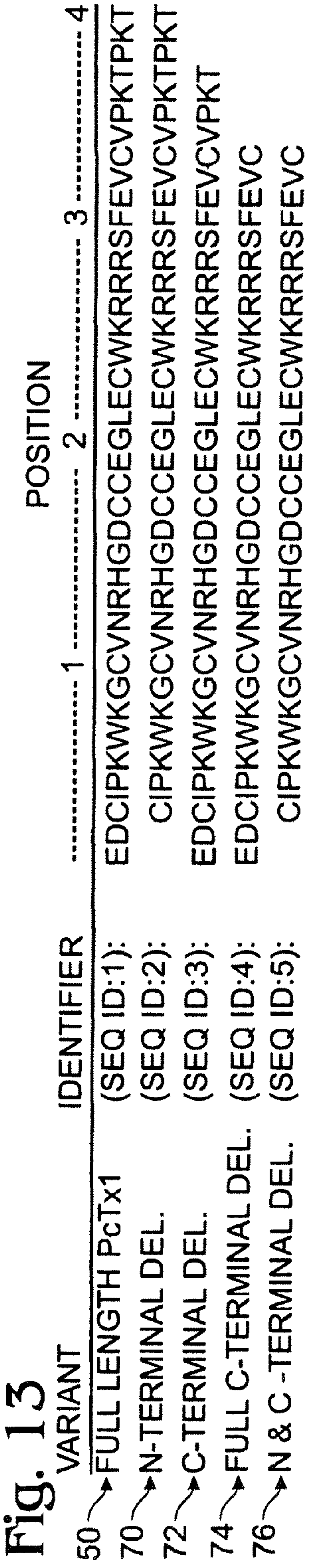
FIG. 13 is a comparative view of the cystine knot peptide of FIG. 12 aligned with various exemplary deletion derivatives of the peptide.

FIG. 13 shows a comparison of the PcTx1 peptide 50 of FIG. 12 aligned with various exemplary deletion derivatives of the peptide. These derivatives may include an N-terminal deletion 70 (SEQ ID NO:2), a partial C-terminal deletion 72 (SEQ ID NO:3), a full C-terminal deletion 74 (SEQ ID NO:4), and an N/C terminal deletion 76 (SEQ ID NO:5). Other derivatives of PcTx1 may include any deletion, insertion, or substitution of one or more amino acids, for example, while maintaining sequence similarity or identity of at least about 25% or about 50% with the original PcTx1 sequence.

Each PcTx1 derivative may be tested for its ability to inhibit ASIC proteins selectively and/or for an effect, if any, on ischemia. Any suitable test system(s) may be used to perform this testing including any of the cell-based assay systems and/or animal model systems described elsewhere in the present teachings. The PcTx1 derivative also or alternatively may be tested in ischemic human subjects.

Example 4: Selectivity of PcTX Venom for ASIC1a

Figure 14:
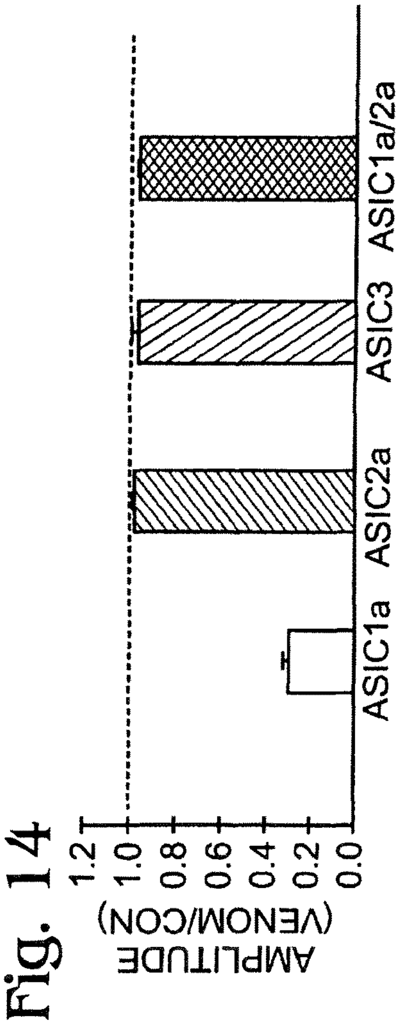
FIG. 14 is an exemplary graph plotting the amplitude of calcium current measured in cells as a function of the ASIC family member(s) expressed in the cells.

This example describes experiments that measure the selectivity of PcTX venom (and thus PcTx1 toxin) for ASIC1a alone, relative to other ASIC proteins or combinations of ASIC proteins expressed in cultured cells. COS-7 cells expressing the indicated ASIC proteins were treated with PcTX venom (25 ng/mL on ASIC1a expressing cells and 500 ng/mL on ASIC2a, ASIC3 or ASIC1a+2a expressing cells). Channel currents were measured at the pH of half maximal channel activation (pH 0.5). As shown in FIG. 14, PcTX venom largely blocked the currents mediated by ASIC1a homomeric channels at a protein concentration of 25 ng/mL, with no effect on the currents mediated by homomeric ASIC2a, ASIC3, or heteromeric ASIC1a/ASIC2a at 500 ng/mL (n=3-6). At 500 ng/mL, PcTX venom also did not affect the currents mediated by other ligand-gated channels (e.g., NMDA and GABA receptor-gated channels) and voltage-gated channels (e.g., Na+, Ca2+, and K+ channels) (n=4-5). These experiments indicate that PcTX venom and thus PcTx1 peptide is a specific inhibitor for homomeric ASIC1a. Using this cell-based assay system, the potency and selectivity of ASIC inhibition may be measured for various synthetic peptides or other candidate inhibitors (e.g., see Example 3).

Example 5: Nasal Administration of PcTX Venom is Neuroprotective

Figure 15:
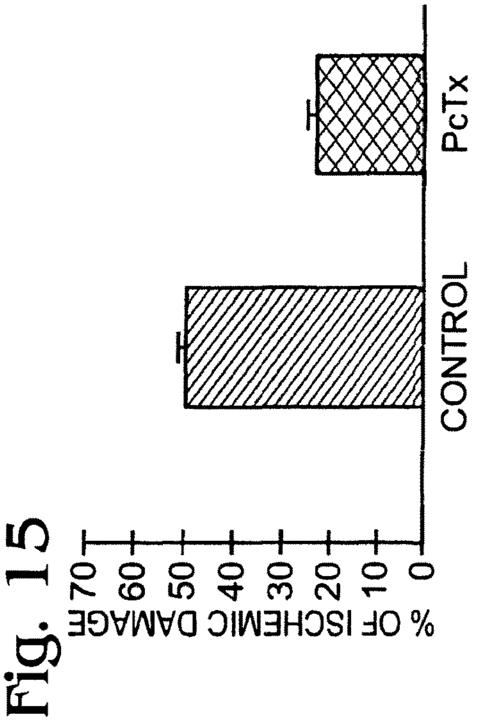
FIG. 15 is a graph presenting exemplary data related to the efficacy of nasally administered PcTx venom in reducing ischemic injury in an animal model system.

This example describes exemplary data indicating the efficacy of nasally administered PcTX venom for reducing ischemia-induced injury in an animal model system of stroke. Cerebral ischemia was induced in male mice by mid-cerebral artery occlusion. One hour after occlusion was initiated animals were treated as controls or were treated with PcTX venom (50 μL of 5 ng/mL (total protein) PcTx venom introduced intranasally). As shown in FIG. 15, nasal administration of PcTX venom resulted in a 55% reduction in ischemia-induced injury (ischemic damage), as defined by infarct volume, relative to control treatment. Nasal administration may be via a spray that is deposited substantially in the nasal passages rather than inhaled into the lungs and/or may be via an aerosol that is at least partially inhaled into the lungs. In some examples, nasal administration may have a number of advantages over other routes of administration, such as more efficient delivery to the brain and/or adaptability for self-administration by an ischemic subject.

Example 6: Inhibition of ASIC1a Channel by Amiloride and Amiloride Analogs

Figure 16A:
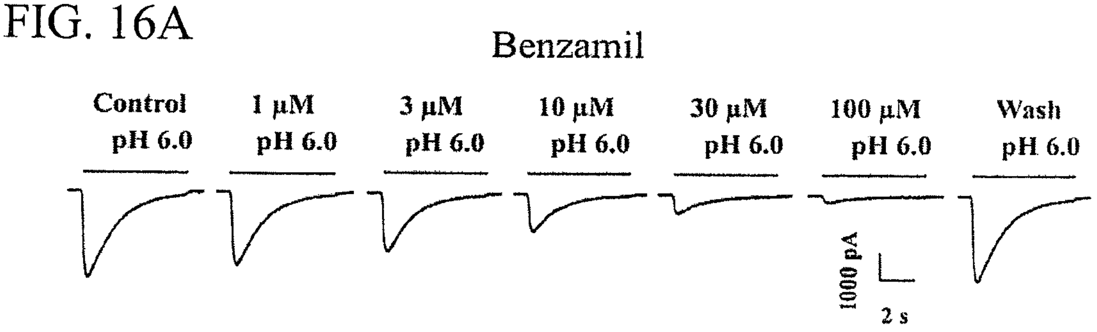
FIGS. 16A-C are a composite showing representative ASIC la current traces in CHO cells treated with benzamil (panel A) or 5-(N-ethyl-N-isopropyl) amiloride (EIPA) (panel B), and dose-dependent blockade of ASIC la current expressed in CHO cells by amiloride and amiloride analogs (panel C).
Figure 16B:
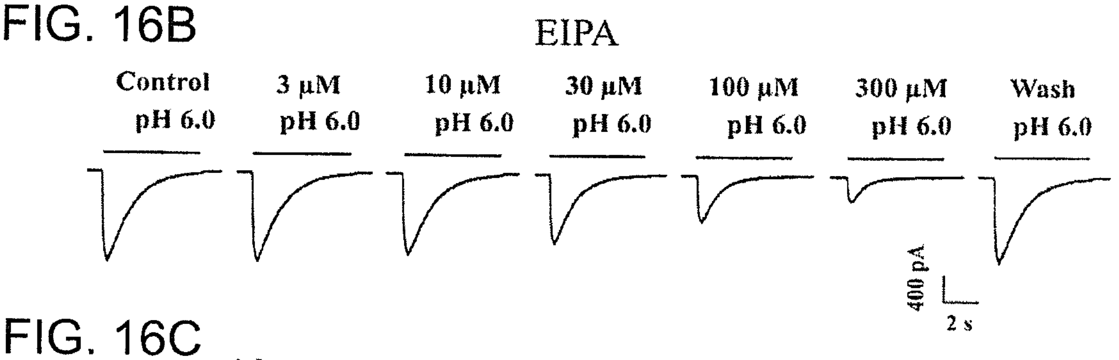
Figure 16C:
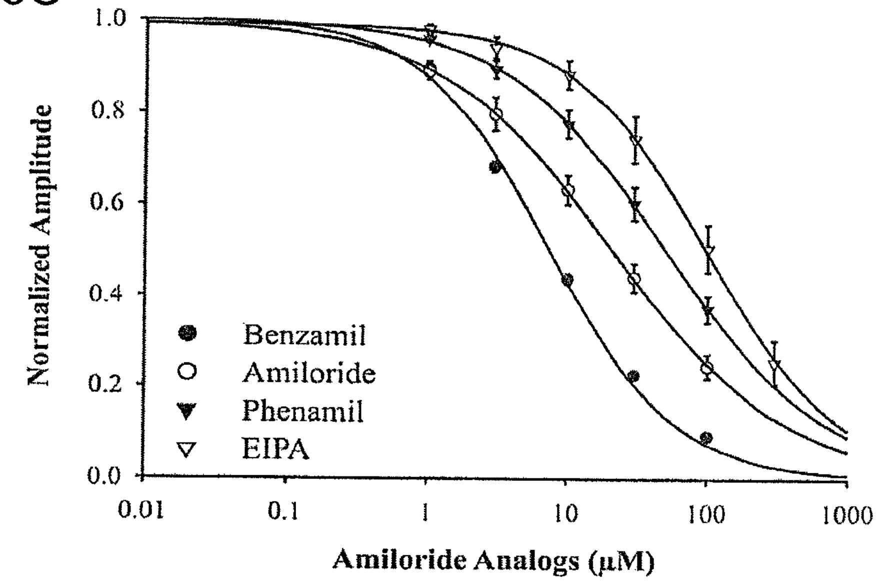
Figures 17A, 17B, 17C:
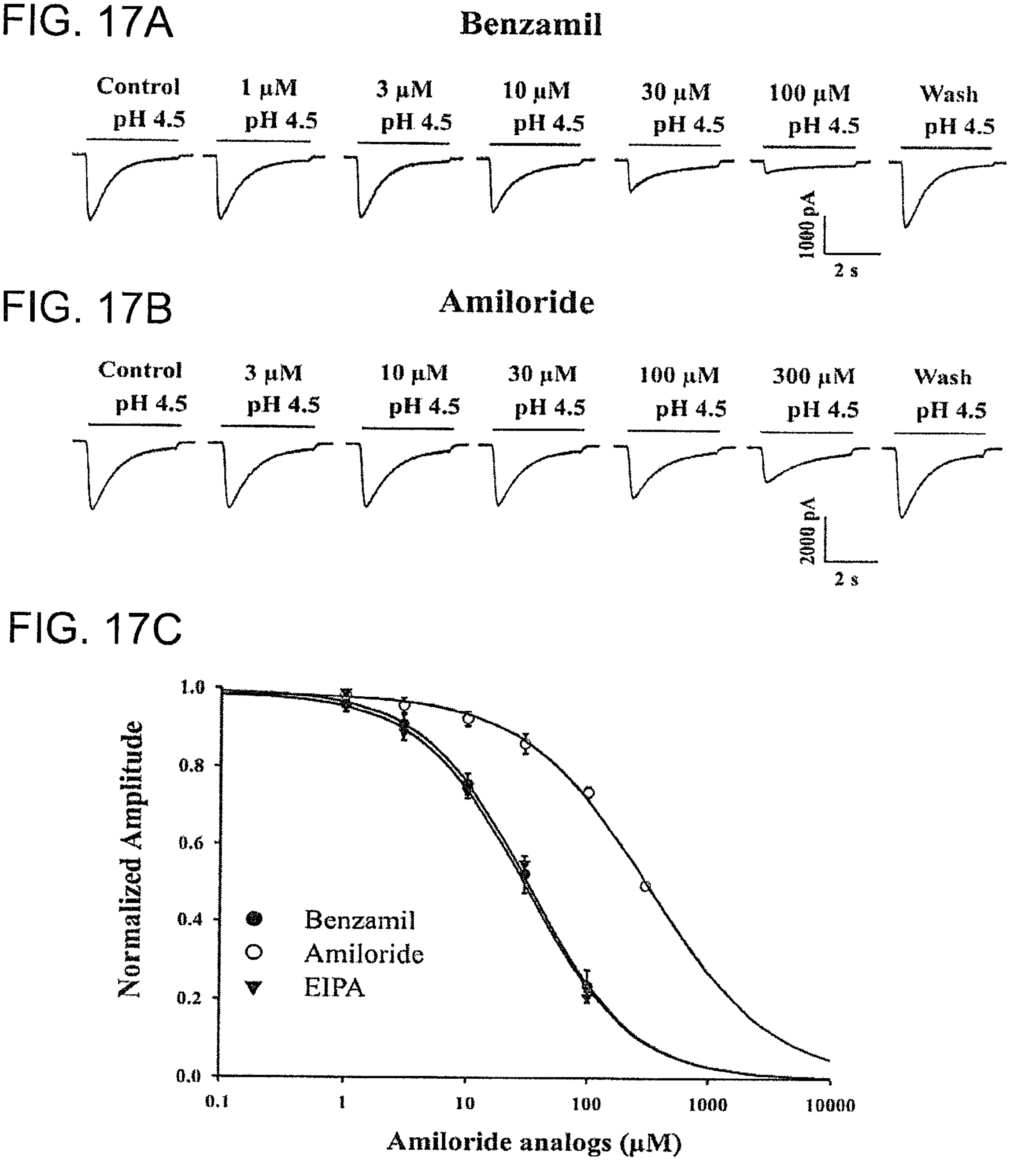
FIGS. 17A-C are a composite showing representative ASIC 2a current traces in CHO cells treated with benzamil (panel A) or amiloride (panel B), and dose-dependent blockade of ASIC 2a current expressed in CHO cells by amiloride and amiloride analogs (panel C).

As shown in FIG. 16, amiloride and amiloride analogs benzamil, phenamil and EIPA block ASIC1a current in a dose-dependent manner. Similarly, amiloride and amiloride analogs benzamil and EIPA block ASIC2a current in a dose-dependent manner (FIG. 17). Table 1 summarizes inhibition of the ASIC1a channel by amiloride and amiloride analogs. Amiloride was an effective inhibitor of this channel with an IC50 of 7.7 μM.

TABLE 1

Inhibition of the ASIC1a channel by amiloride and amiloride analogs.

| | | | |
|---|---|---|---|
| Knockout 1a | 39.1 ± 3.8 | (n = 4) | |
| Knockout 2a | 5.14 ± 0.79 | (n = 5) | |
| Neuron (−60 mV) | 43.3 ± 1.4 | (n = 6) | EIPA |
| Neuron (−20 mV) | 32.2 ± 6.3 | (n = 3) | |
| CHO 1a | 111 ± 30 | (n = 5) | |
| CHO 2a | 31 | (n = 1) | |
| Knockout 1a | 35.9 ± 2.1 | (n = 5) | |
| Knockout 2a | 20.1 ± 2.2 | (n = 2) | |
| Neuron (−60 mV) | 82.9 ± 5.2 | (n = 8) | Bepridil |
| Neuron (−60 mV) | 100 ± 11 | (n = 10) | KB-R7943 |
| Neuron (−60 mV) | 24.3 ± 17.2 | (n = 2) | 5-(N-methyl-N-isobutyl) amiloride |

TABLE 1-continued

| Inhibition of the ASIC1a channel by amiloride and amiloride analogs. | | |
|---|---|---|
| Neuron (−60 mV) | 15.0 ± 11.7 (n = 3) | 5-(N,N-hexamethylene) amiloride |
| Neuron (−60 mV) | 14.8 ± 7.1 (n = 2) | 5-(N,N-dimethyl) amiloride hydrochloride |

Figure 18:
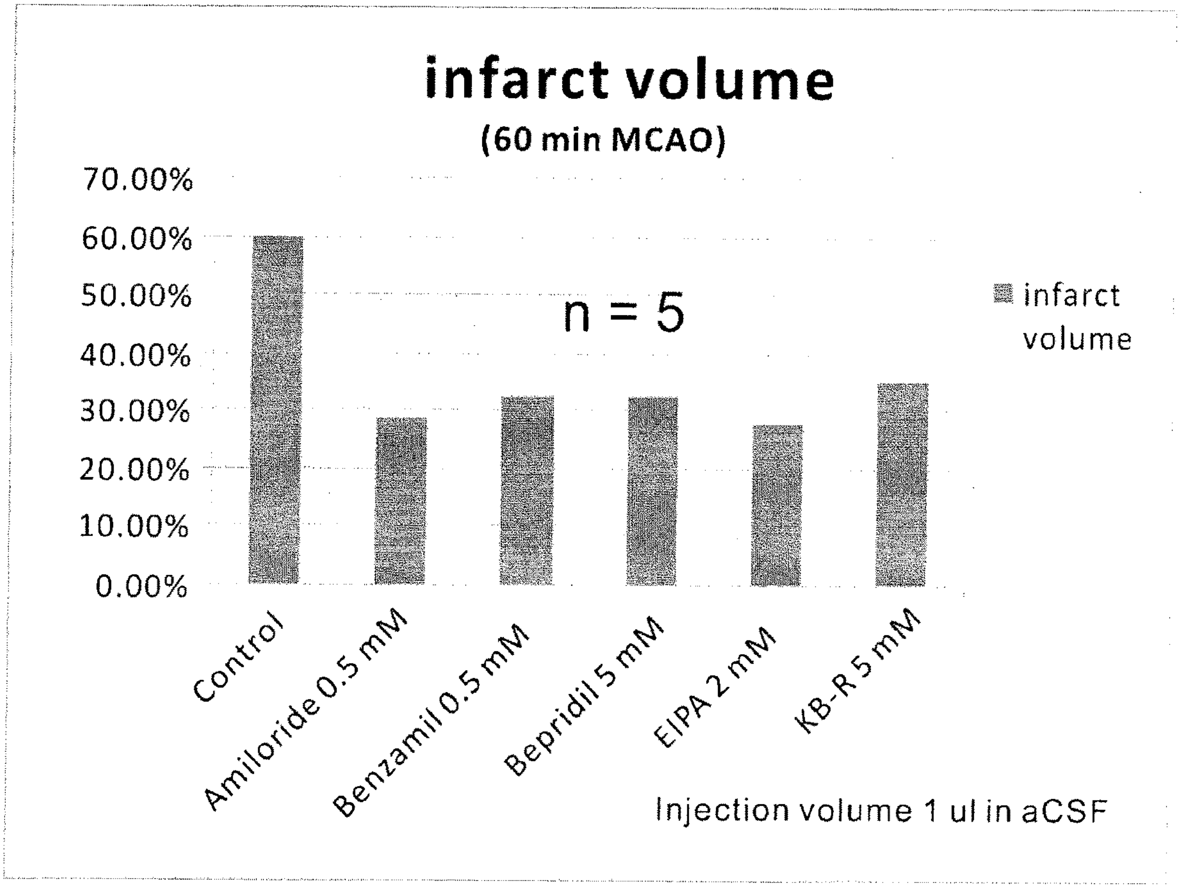
FIG. 18 is a graph showing reduction of infarct volume in mice by intracerebroventricular injections of amiloride or amiloride analogs.

Example 7: Reduction of Infarct Volume in Mice by Intracerebroventricular Injection of Amiloride and Amiloride Analogs Mice were subjected to 60 minutes of middle cerebral artery occlusion (MCAO) as described above. Amiloride or an amiloride analog benzamil, bepridil, EIPA or KB-R7943 was administered by intracerebroventricular injection one hour after MCAO. The animals were evaluated one day after ischemia induction. As shown in FIG. 18, intracerebroventricular injection of amiloride or an amiloride analog benzamil, bepridil, EIPA or KB-R7943 effectively reduce infarct volume.

Figure 19:
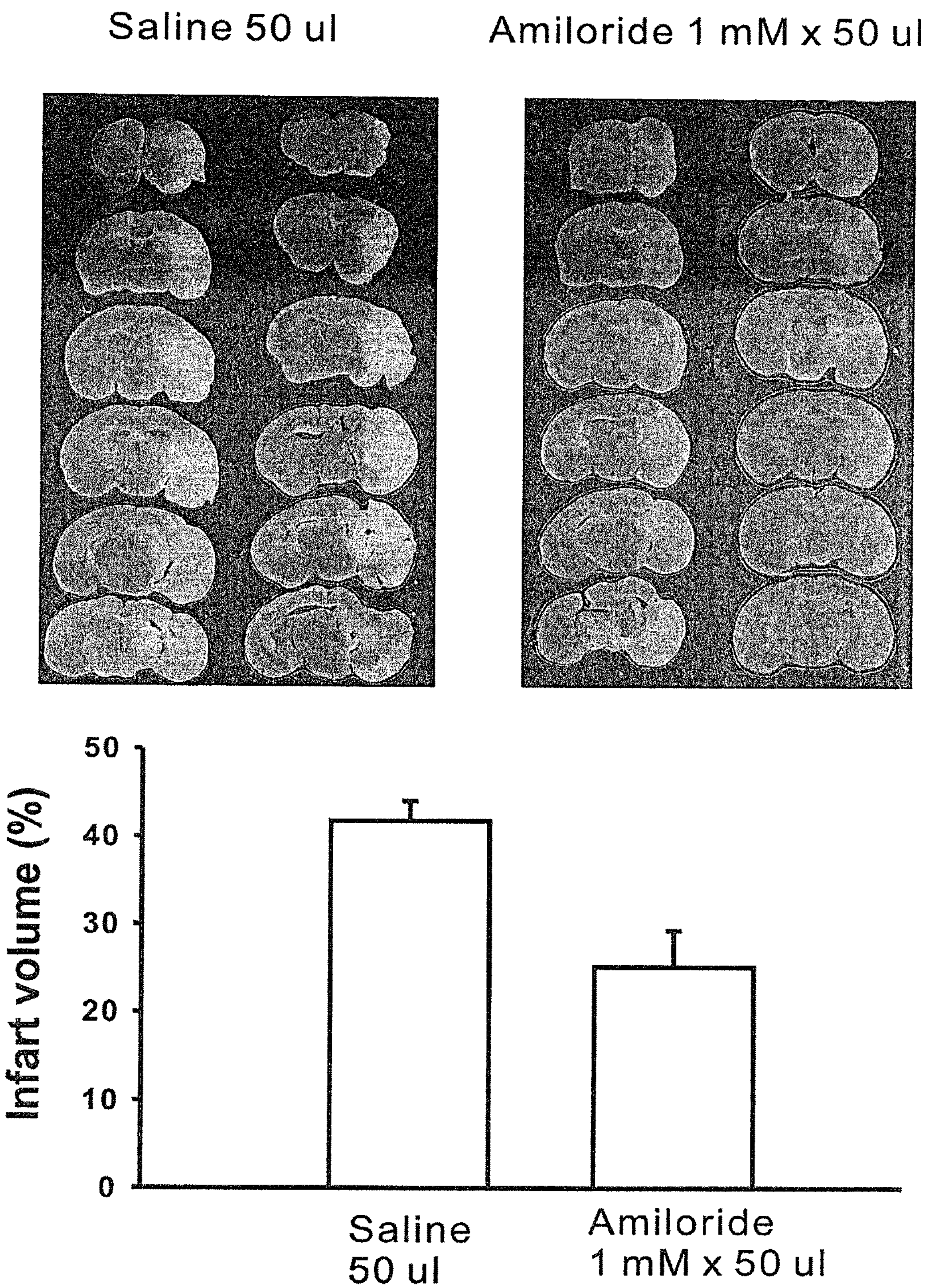
FIG. 19 is a composite showing reduction of infarct volume in the cortical tissue of mice by intravenous injection of saline or amiloride 60 min after MCAO.
Figure 20:
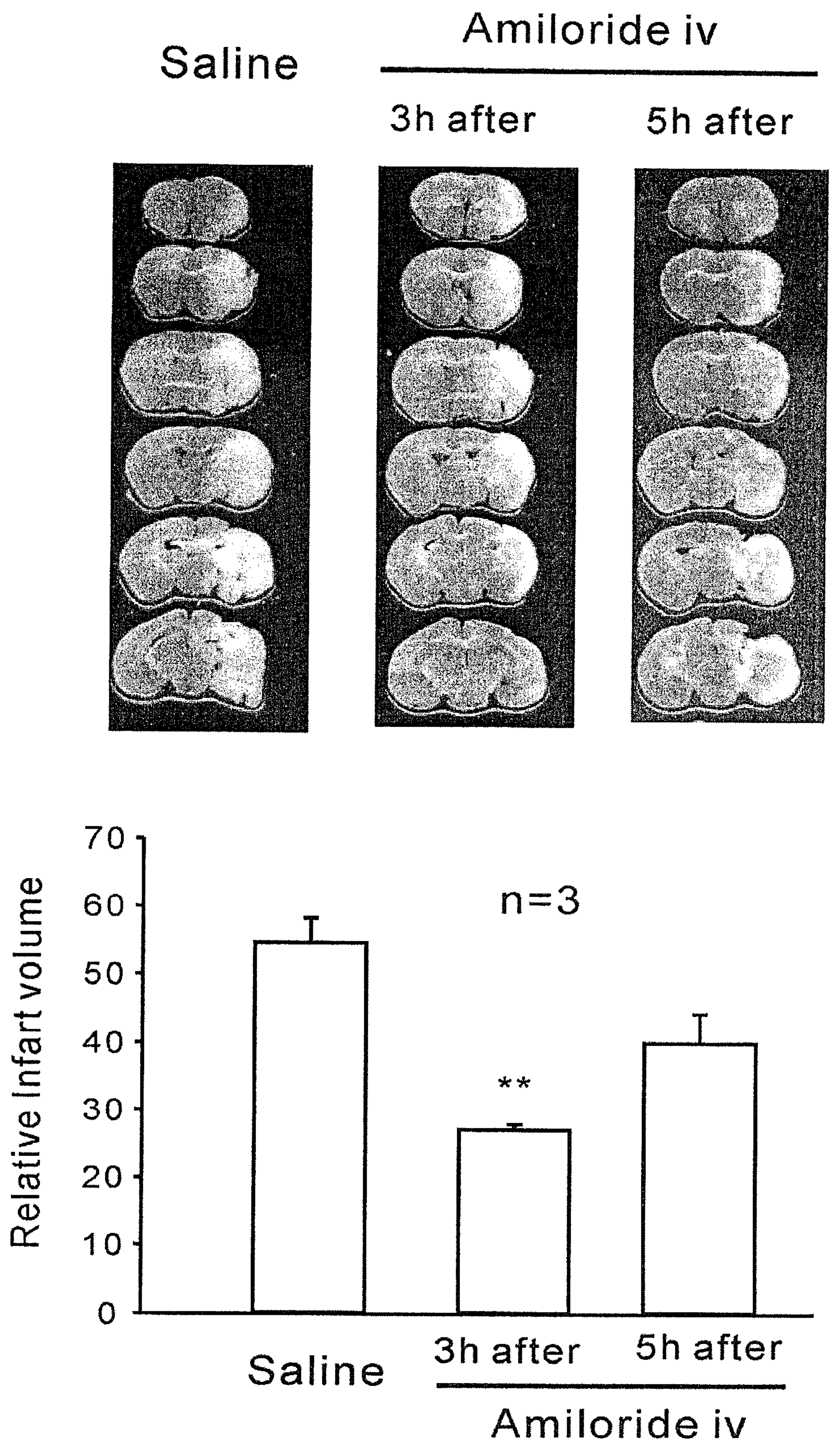
FIG. 20 is a composite showing reduction of infarct volume in the cortical tissue of mice by intravenous injection of saline or amiloride 3 hours or 5 hours after MCAO.

Example 8: Reduction of Infarct Volume in Mice by Intravenous Injection of Amiloride Mice were subjected to 60 minutes of middle cerebral artery occlusion (MCAO) as described above. Amiloride was administered by intravenous injection 1, 3 or 5 hours after MCAO. The animals were evaluated one day after ischemia induction. As shown in FIG. 19, intravenous injection of amiloride effectively reduces infarct volume. The effective CNS penetration of amiloride may be explained by the fact that blood-brain-barrier is compromised following brain ischemia/reperfusion. FIG. 20 shows that intravenous injection of amiloride has a prolonged therapeutic window of 5 h.

Example 9: Structure Activity Relationships for Hydrophobic Amiloride Analogs on Various Channels As shown in Table 1, substituting the C-5 amino group in amiloride with alkyl groups led to a decrease in potency at the ASIC1a channel. The same substitution increases potency to the ASIC3 channel (Kuduk et al., Bioorg. Med. Chem. Lett., 2009, 19:2514-2518). The reverse result was obtained when substituting hydrophobic groups onto the guanidino part of the structure. Indeed, the benzyl substituted guanidino analog, benzamil, was the most potent ASIC1a blocking compound tested (IC50=4.9 μM). Taken together, these results showed that amiloride is an effective inhibitor of ASUC1a with an $IC_{50}$ of 7.7 μM. They also provide structure activity relationships (see FIG. 21) for designing amiloride analogs that would inhibit the ASIC1a channel. Accordingly, in some embodiments, amiloride analogs are generated by introducing changes in the guanidine portion of the amiloride structure. Since amiloride is only a very weak inhibitor of the $Na^{-}/Ca^{2+}$ ion exchanger ($IC_{50}$=1.1 mM). The amiloride analogs are likely be a very weak inhibitor of the $Na^{+}/Ca^{2+}$ ion exchanger as well. In some embodiments, the amiloride analogs are designed to have increased selectivity for ASIC1a over the ASIC3 channel. In other embodiments, a ring structure, such as a cyclic guanidine group, is introduced into the amiloride structure to increase inhibitory potency of ASIC1a currents.

It is also possible that one or more of the N—H groups of amiloride will form H-bonds either internally with the 3-amino group or with the ion channel.

The in vivo results in mice showed that efficacy can be achieved with a plasma concentration of 32.5 μM (iv dose of 50 μl×1mM) and a total brain concentration of 12.5 μM (icy dose of 1μl×500 μM). It is thus estimated that only a 10-fold increase in potency is necessary to achieve efficacious concentrations that are suitable for an acute therapeutic for stroke in humans. Therefore, novel analogs are screened for an increased ASIC1a IC50 potency from the 4 to 8 μM for amiloride and benzamil to <1 μM.

In some embodiments, the amiloride analogs comprise methylated analogs of benzamil (formula 1-5 of FIG. 21) and amidino analog of benzamil (formula 6 of FIG. 21). In other embodiments, the amiloride analogs contain a ring formed on the guanidine group. In other embodiments, the amiloride analogs contain an acylguanidino group for increased inhibitory potency of ASIC1a currents.

Amiloride is soluble in water at 1 mM and is effective in treating ischemia in a mouse model at a dose of 50 ul per injection. The equivalent dose on a mg/kg basis in a 65 kg human would be close to 40 mg and require an injection volume of over 160 ml. Similarly benzamil has a reported solubility in 0.9% saline of 0.4mg/ml (1.7 mM), which permits administration of only 5 mg benzamil dihydrochloride in a 10 ml injection. Accordingly, amiloride analogs with higher water solubility are desired. In some embodiments, the amiloride analogs contain a water solubilizing group, such as an N,N-dimethyl amino group or a sugar, at the guanidino group to improve water solubility. In some embodiments, the amiloride analogs have a water solubility of 5 mM, 10 mM, 20 mM, 30 mM, 40 mM, 50 mM, 60 mM, 70 mM, 80 mM, 90 mM, 100 mM or higher. In other embodiments, the amiloride analogs have a solubility that allows for a 10 mg, 25 mg, 50 mg, 100 mg, 150 mg, 200 mg, 250 mg, 300 mg, 400 mg, or 500 mg dose to be administered intravenously to a human in a single 10 ml injection. In yet other embodiments, the amiloride analogs have a solubility that allows for a 10 mg, 25 mg, 50 mg, 100 mg, 150 mg, 200 mg, 250 mg, 300 mg, 400 mg, or 500 mg dose to be administered intracerebroventicularly to a human in a single 2 ml injection.

Example 10: Use of Amiloride and Amiloride Analogues in Transient Ischemic Attack Model To evaluate the neuroprotective potential of amiloride and its analogs, a transient focal ischemia model in mice (Li et al., Brain Research, 1055:180-185, 2005; Pedrono et al., J. Neuropathol Exp. Neurol., 69(2):188-195, 2010) or rats (Tolvanen et al., Brain Research, 1663:166-173, 2017) is employed with or without the anti-clotting agents described herein. Prior to induction of transient focal ischemia, animals are pre-treated for 5-10 days with amiloride, amiloride analogs, and/or anti-clotting agents by gavage or intraperitoneal injection (e.g., 1-60 mg/kg/day each). Middle cerebral artery occlusion (MCAO) is induced using an intraluminal monofilament. The tip of a surgical suture (6-0 nylon monofilament, Ethicon, UK) is blunted or rounded by heating, introduced into the common carotid artery (CCA) and then advanced intracranially to the origin of the middle cerebral artery (MCA) to block the blood flow into that artery. After the insertion of the monofilament (thereby the start of the MCA occlusion), the monofilament was secured in place for a period of 5-10 min. After that period of MCAO, the monofilament was withdrawn to allow reperfusion into the MCA for 24 hours. Under these conditions, no detectable brain infarction is expected.

The effects of the active agents on % hemispheric lesion volume, brain oedema, rotarod performance, spontaneous locomotor activity and mortality rate are assessed. The NMDA channel blocker and gold standard NMDA antagonist, MK-801 may be used as a control.

Regional cerebral blood flow (CBF) is measured in animals by laser Doppler flowmetry (LDF) by applying a flexible fiber-optic probe onto the intact and bare cranial surface on the territory receiving blood supply from the MCA (1 mm posterior and 3 mm lateral to the bregma). Cerebral blood flow values at baseline, occlusion, and reperfusion (immediately, and at 10, 20, 30, and 24 hours after reperfusion) are recorded.

At the end of the reperfusion period (i.e., at 24 hours), the functional consequences of the transient ischemic insult are evaluated using a 5-point scale of neurological status (or sensorimotor skills) as follows: 0, no deficit; 1, failure to fully extend the left or right paw; 2, circling to the left or right; 3, decreased resistance to lateral push; 4, unable to walk spontaneously.

Following reperfusion and evaluation of neurological status, the animals are sacrificed and their brains are harvested, fixed in formaldehyde, and embedded in paraffin blocks. 4-6 μm-thick sections are cut with a microtome and are subjected to staining with hematoxylin and eosin (H&E), immunohistochemical staining (e.g., fibrinogen, glycoprotein 1 beta (GP1b) for detection of thrombus development) and/or apoptosis staining (e.g., TUNEL kit; (In Situ Cell Death Detection Kit, Fluorescein; Sigma-Aldrich, St. Louis, Mo.). The above-described assays are used to demonstrate the extent of ischemic changes and to correlate these changes with the prophylactic benefits conferred by ASIC1a inhibition, with or without anti-clotting agents described in the present disclosure.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for reducing the incidence of a transient ischemic attack in a subject at risk for developing a stroke, comprising:

administering to the subject a prophylactically effective amount of a pharmaceutical composition comprising an ASIC1a inhibitor capable of penetrating the blood-brain barrier.

2. The method of claim 1, wherein the ASIC1a inhibitor comprises amiloride, an amiloride analog, or a pharmaceutically acceptable salt thereof.

3. The method of claim 1, wherein the ASIC1a inhibitor comprises amiloride or a pharmaceutically acceptable salt thereof.

4. The method of claim 1, wherein the ASIC1a inhibitor comprises an amiloride analog or a pharmaceutically acceptable salt thereof.

5. The method of claim 4, wherein the amiloride analog is selected from the group consisting of benzamil, bepridil, KB-R7943, phenamil, 5-(N-N-dimethyl) amiloride (DMA), 5-(N,N-hexamethylene) amiloride (HMA), 5-(N-ethyl-N-isopropyl)-amiloride (EIPA), 5-(N-methyl-N-isobutyl) amiloride (MIA), pharmaceutically acceptable salts or solvates thereof, methylated analogs thereof, and combinations thereof.

6. The method of claim 4, wherein the amiloride analog is selected from the group consisting of methylated analogs of benzamil, amiloride analogs containing a ring formed on a guanidine group, amiloride analogs containing an acylguanidino group, and amiloride analogs containing a water solubilizing group formed on a guanidine group, wherein the water solubilizing group is a N,N-dimethyl amino group or a sugar group.

7. The method of claim 1, wherein the pharmaceutical composition is administered daily.

8. The method of claim 1, wherein the pharmaceutical composition is formulated as an extended release formulation.

9. The method of claim 1, wherein the subject has recently had heart surgery or has previously had a TIA or stroke.

10. The method of claim 1, wherein the subject has an abnormal heart rhythm selected from the group consisting of atrial fibrillation, atrial flutter, ventricular tachycardia, and ventricular fibrillation.

11. The method of claim 1, wherein the subject has acute coronary syndrome, arterial embolism, atherosclerosis, atrial fibrillation, carotid artery disease, cerebral arterial thrombosis, cerebral embolism, coronary arterial thrombosis, coronary heart disease, deep vein thrombosis, kidney embolism, myocardial infarction, peripheral arteriopathy, pulmonary embolism, stroke, thrombophlebitis, thrombosis, transient ischemic attack, unstable angina, valvular heart disease, venous thrombosis, ventricular fibrillation, or a combination thereof.

12. The method of claim 1, wherein the amiloride, amiloride analog or a pharmaceutically acceptable salt or solvate thereof is administered in a dose range of 0.1 mg-10 mg/kg body weight.

13. The method of claim 1, further comprising administering to the subject one or more anti-clotting agents.

14. The method of claim 13, wherein the one or more anti-clotting agents comprise an antiplatelet agent selected from the group consisting of aspirin, clopidogrel, prasugrel, ticagrelor, dipyridamole, and combinations thereof.

15. The method of claim 13, wherein the one or more anti-clotting agents comprise an anticoagulant selected from the group consisting of vitamin-K epoxide reductase inhibitors, direct thrombin inhibitors and direct Factor Xa inhibitors.

16. The method of claim 13, wherein the one or more anti-clotting agents comprise an anticoagulant selected from the group consisting of apixaban, argatroban, AZD-0837, betrixaban, dabigatran, edoxaban, heparin, rivoraxaban, tecarfarin, warfarin, ximelagatran, YM466, and combinations thereof.

17. The method of claim 1, further comprising administering to the subject an anti-arrhythmic agent selected from the group consisting of amiodarone, AZD-1305, budiodarone, celivarone, dofetilide, dronedarone, flecainide, ibutilide, propafenone, quinidine, sotolol, vernakalant, and combinations thereof.

18. The method of claim 1, wherein the pharmaceutical composition is administered intravenously or intramuscularly.

* * * * *

```
                              SEQUENCE LISTING


<160> NUMBER OF SEQ ID NOS: 5

<210> SEQ ID NO 1
<211> LENGTH: 40
<212> TYPE: PRT
<213> ORGANISM: Psalmopoeus cambridgei
<300> PUBLICATION INFORMATION:
<301> AUTHORS: Escoubas P., de Weille J.R., Lecoq A., Diochot S.,
      Waldmann R., Champigny G., Moinier D., Menez A., Lazdunski M.
<302> TITLE: Isolation of a tarantula toxin specific for a class of
      proton-gated Na+ channels
<303> JOURNAL: J. Biol. Chem.
<304> VOLUME: 275
<306> PAGES: 25116-25121
<307> DATE: 2000-08-18
<313> RELEVANT RESIDUES IN SEQ ID NO: (1)..(40)
<300> PUBLICATION INFORMATION:
<308> DATABASE ACCESSION NUMBER: SWISSPROT / P60514
<309> DATABASE ENTRY DATE: 2004-03-29
<313> RELEVANT RESIDUES IN SEQ ID NO: (1)..(40)

<400> SEQUENCE: 1

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr Pro Lys Thr
        35                  40


<210> SEQ ID NO 2
<211> LENGTH: 38
<212> TYPE: PRT
<213> ORGANISM: Artificial
<220> FEATURE:
<223> OTHER INFORMATION: Deletion derivative of PcTx1 (SEQ ID NO:1)

<400> SEQUENCE: 2

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys Val
```

-continued

```
            20                  25                  30

Pro Lys Thr Pro Lys Thr
        35


<210> SEQ ID NO 3
<211> LENGTH: 37
<212> TYPE: PRT
<213> ORGANISM: Artificial
<220> FEATURE:
<223> OTHER INFORMATION: Deletion derivative of PcTx1 (SEQ ID NO:1)

<400> SEQUENCE: 3

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys Val Pro Lys Thr
        35


<210> SEQ ID NO 4
<211> LENGTH: 33
<212> TYPE: PRT
<213> ORGANISM: Artificial
<220> FEATURE:
<223> OTHER INFORMATION: Deletion derivative of PcTx1 (SEQ ID NO:1)

<400> SEQUENCE: 4

Glu Asp Cys Ile Pro Lys Trp Lys Gly Cys Val Asn Arg His Gly Asp
1               5                   10                  15

Cys Cys Glu Gly Leu Glu Cys Trp Lys Arg Arg Arg Ser Phe Glu Val
            20                  25                  30

Cys


<210> SEQ ID NO 5
<211> LENGTH: 31
<212> TYPE: PRT
<213> ORGANISM: Artificial
<220> FEATURE:
<223> OTHER INFORMATION: Deletion derivative of PcTx1 (SEQ ID NO:1)

<400> SEQUENCE: 5

Cys Ile Pro Lys Trp Lys Gly Cys Val Asn Arg His Gly Asp Cys Cys
1               5                   10                  15

Glu Gly Leu Glu Cys Trp Lys Arg Arg Arg Ser Phe Glu Val Cys
            20                  25                  30
```